United States Patent [19]

Campbell

[11] Patent Number: 5,420,328

[45] Date of Patent: May 30, 1995

[54] METHODS FOR THE SYNTHESIS OF PHOSPHONATE ESTERS

[75] Inventor: David A. Campbell, Redwood Shores, Calif.

[73] Assignee: Affymax Technologies, N.V., Caracao, Netherlands Antilles

[21] Appl. No.: 119,700

[22] Filed: Sep. 9, 1993

Related U.S. Application Data

[63] Continuation-in-part of Ser. No. 81,577, Jun. 21, 1993, abandoned, which is a continuation-in-part of Ser. No. 943,805, Sep. 11, 1992, Pat. No. 5,359,115.

[51] Int. Cl.$^6$ .................................. C07F 9/09
[52] U.S. Cl. ...................................... 558/110
[58] Field of Search .......................... 558/110

[56] References Cited

U.S. PATENT DOCUMENTS 5,143,854  9/1992  Pirrung et al. ................... 436/518
5,183,810  2/1993  Greenlee et al .................. 514/63

OTHER PUBLICATIONS

Gilmore et al., 1974, J. Pharm. Sci. 63: 965–966 New compounds: Monoesters of a-Aminobenzylphosphonic Acid.

Loibner and Zbiral, 1976, Helvetica Chimica Acta 59 (6): 2100–2113 Reaktionen mit phosphororganischen Verbindungen.XLI[1]') Neuartige synthetische Aspekte des systems Triphenylphoshin–Azodicarbonsaurees-ter–Hydroxyverbindung.

Kurihara et al., 1976, Tetrahedron Ltrs. 28: 2455–2458 Synthesis of lactones and cycloalkanes. Cyclization of w–hydroxy acids and ethyl a–cyano–w–hydroxycar-boxylates.

Wasielewski et al., 1976, J. Rocz. Chem. 50: 1613–1620 Aminophosphonic acids, part VIII. application of trichloroacetonitrile for preparation of a–aminophosphonic acid monoesters.

Balthazor and Flores, 1980, J. Org. Chem. 45: 529–531 Dipolar Cycloadditions of an Acetylenic phosphinate.

Mitsunobu, 1981, Synthesis pp. 1–28 The Use of Diethyl Azodicarboxylate and Triphenylphosphine in Synthesis and Transformation of Natural Products.

Vargas et al., 1984, Biochim. Biophys. Acta 796: 123–128 Inhibition of Platelet phosphatidylinositol synthetase by an analog of CDP-Diacylglycerol.

Karanewsky and Badia, 1986, Tetrahedron Ltrs. 27 (16): 1751–1754 Synthesis of phosphonic monoesters from phosphonous.

Hoffmann, Jul. 1986, Communications: Synthesis, pp. 557–559 A convenient synthesis of alkyl Hydrogen 1-(Benzyloxycarbonylamino)-alkanephosphonates.

Pollack et al., 19 Dec. 1986, Science 234: 1570–1573 Selective Chemical Catalysis by an Antibody.

Tramontano et al., 19 Dec. 1986, Science 234: 1566–1570 Catalytic Antibodies.

Blackburn et al., 1987, Nucl. Acids Res. 15: 6991–7004 Synthesis and resistance to enzymic hydrolysis of stereochemically–defined phosphonate and thiophosphate analogues of P1,P4-bis (5'-adenosyl)-tetraphosphate.

Norbeck et al., 1987, J. Org. Chem. 52: 2174–2179 Synthesis of an Isoteric Phosphonate Analogue of Cytidine 5'-Monophospho—3-deoxy-D-manno-2-octulosonic Acid.

Jacobs et al., 1 Apr. 1987, J. Amer. Chem. Soc. 109: 2174–2176 Catalytic Antibodies.

(List continued on next page.)

*Primary Examiner*—Mary C. Lee
*Assistant Examiner*—Michael G. Ambrose
*Attorney, Agent, or Firm*—Kevin Kaster; Vern Norviel; Lauren L. Stevens

[57] ABSTRACT

Phsophonate esters can be synthesized in high yields by condensations of alcohols with methyl phosphonates followed by selective demethylation. The reaction is general, relativly insensitive to steric constraints of hindered phosphonic acids, and can also be carried out on a solid support to synthesize large collections of compounds to screen for pharmacological activity.

11 Claims, 10 Drawing Sheets

OTHER PUBLICATIONS

Biller et al., Oct. 1988, J. Medicinal Chemistry 31 (10): 1869–1871 Isoprenoid (Phosphinylmethyl) phosphonates as inhibitors of squalene synthetase.

Bartlett et al., 1990, J. Org. Chem. 55 (26): 6268–6274 Potent Inhibitions of Pepsin and Penicillopepsin by Phosphorus–Containing Peptide Analogues.

Kaplan et al., 1991, Biochemistry 30 (33): 8165–8170 Synthesis and Evaluation of an Inhibitor of Carboxypeptidase A with a Ki Value in the Femtomolar Range.

Morgan et al., 1991, J. Am. Chem. Soc. 113 (1): 297–307 Differential binding energy: a detailed evaluation of the influence of hydrogen–bonding and hydrophobic groups on the inhibition of thermolysin by phosphorus–containing inhibitors.

Kimura et al., 1979, Bull. Chem. Soc. Japan 52(4): 1191–1196 Studies on nucleosides and nucleotides. VII. Preparation of pyrimidine nucleoside 5'–Phosphonates and.

SCHEME I. a) NaNO2, CITRIC OR ACETIC ACID, DIOXANE, H2O, 0°C;
b) (1) TRIISOPROPYLSILYL CHLORIDE, N-METHYLMORPHOLINE, PYRIDINE, (2) FMOC-Cl, N-METHYLMORPHOLINE, (3) TETRABUTYLAMMONIUM FLUORIDE

REAGENTS: i) AMINO ACID, HBTU, HOBT, DIEA, NMP; ii) 30% PIPERIDINE/NMP; iii) α-O-FMOC-HYDROXY ACID, HBTU, HOBT, DIEA, NMP; iv) METHYL, α-N-NPEOC-AMINOALKYLPHOSPHONATE, TRIS(4-CHLOROPHENYL)PHOSPHINE, DIAD, DIEA, THF; v) 5% DBU/NMP; vi) THIOPHENOL, TEA, DIOXANE; vii) TFA, SCAVENGERS, DCM.
* SYNTHESIS CYCLE SHOWN WITH AMIDE RESIN, COUPLING CHEMISTRY IS ALSO COMPATIBLE WITH ACID RESINS.

4.1) REMOVE ALIQUOT (30 ul) FROM EACH VIAL AND COMBINE IN ONE CENTRAL VIAL (TOTAL VOLUME = 150 ul); VORTEX—THIS LEAVES APPROXIMATELY 20 ul BEHIND IN EACH VIAL, WASH THIS MATERIAL (1.6 mg BEADS) WITH ETHER (5X); DRY; STORE FOR LATER USE.

4.2) TRANSFER ALIQUOTS (25 ul) INTO SIX SEPARATE VIALS.

5.1) CENTRIFUGE VIALS, WASH WITH ETHER (3X), DRY UNDER VACUUM OVERNIGHT WITH $P_2O_5$.

5.2) PERFORM MITSUNOBU REACTION WITH A DIFFERENT NPEOC-PHOSPHONIC ACID (APPROXIMATELY 10 mg OF ACID SCALE)/VIAL. SONICATE AT 25°C ALL DAY.

5.3) CENTRIFUGE VIALS, REMOVE SUPERNATANT, REPEAT # 5.2, SONICATE OVERNIGHT.

5.4) WASH RESIN WITH NMP (5X); ETHER (3X); DRY IN HEATER BLOCK 5.5) DEPROTECT NPEOC WITH 5% DBU/NMP (250 ul) FOR 2-HOURS.

5.6) ASSAY 308 nm: SUPERNATANT (50ul)/NMP (450 ul).

5.7) WASH RESIN WITH NMP (5X); ETHER (3X); DRY 5.8) WITH 10% CBZ-CI/MeCN PLUS PHARMACIA CAPPING REAGENTS A & B2; RATIO 2:1:2 (2 X 30 MINUTES)

5.9) NINHYDRIN TEST SMALL AMOUNT OF RESIN. IF POSITIVE REPEAT CBZ-CI CAPPING TIL NEGATIVE.

5.10) DEMETHYLATE METHYL PHOSPHONATE WITH THIOPHENOL: TRIETHYLAMINE:DIOXANE, 1:2:2 FOR 2-HOUR, WASH BEADS WITH NMP (5X), MeOH (3X), ETHER (3X); DRY IN HEATER BLOCK.

5.11) DEPROTECT RESIN BY TREATING EACH VIAL WITH CLEAVAGE MIXTURE B AS PER INSTRUCTIONS.

5.12) STORE EACH VIAL SEPARATELY, AND WE'LL ASSAY THEM!

FIG. 10B

MONOMER BASIS SET

P₁ | P₁' | P₂'
---|---|---
 |  | 19 AMINO ACIDS (NO CYS)
 |  |
 |  |
 |  |
 |  |

METHODS FOR THE SYNTHESIS OF PHOSPHONATE ESTERS

CROSS-REFERENCE

This application is a continuation-in-part of U.S. patent application Ser. No. 08/081,577, filed Jun. 21, 1993, abandoned, which is a continuation-in-part of copending U.S. patent application Ser. No. 07/943,805, filed Sep. 11, 1992, U.S. Pat. No. 5,359,115. Both of these applications are expressly incorporated herein by reference for all purposes.

This application is also related to copending U.S. patent application Ser. No. 08/120,007, which is incorporated herein by reference for all purposes.

BACKGROUND OF THE INVENTION

This invention relates generally to methods for the synthesis of phosphonate esters. More particularly, the invention provides methods for producing monoesters and diesters of phosphonic acids from condensations of alcohols with alkylphosphonates, such as methyl α-aminoalkyl-phosphonates. The methods can be carried out in solution phase, but in an important embodiment, the method is carried out on a solid support, such as beads or a glass slide, and used to create large arrays of diverse compounds, such as peptidylphosphonates and polyphosphonates, which can then be conveniently screened for the presence of compounds with desired pharmacological or other properties. The invention therefore relates to the fields of chemistry, enzymology, pharmacology, and medicinal chemistry.

Aminophosphonic acids and aminophosphonates are derivatives of amino acids in which the amino acid carboxyl group has been replaced with a phosphonic acid or phosphonate moiety. In α-aminophosphonic acids and phosphonates, the α-carbon is often a chiral center, bearing a phosphonate moiety, an amine moiety, and one or more amino acid side chains. The structure can be represented as follows:

wherein R represents any amino acid side chain and R' and R" represent hydrogen (in the case of a phosphonic acid) or a group such as alkyl or aryl (in the case of a phosphonate ester).

α-Aminophosphonates are used in the synthesis of peptide analogues (peptidylphosphonates) possessing a phosphonate linkage in the place of at least one amide link in the peptide main chain. The phosphonate linkage can impart various useful properties to peptides. Because the phosphonate linkage in a peptidylphosphonate exists as a charged moiety in the peptide backbone, it increases the water solubility of the peptide. Further, the phosphonate linkage can impart protease resistance and thereby increase the serum half-life of many therapeutic peptide. Still further, substitution of the phosphonate linkage for the amide linkage allows additional functionalities to be introduced in otherwise inaccessible regions of naturally occurring peptides. This is because the phosphonate linkages are tetrahedral, while amide linkages are planar. The tetrahedral geometry allows substituents to be placed above and below the plane of the amide linkage of a peptide. Moreover, the tetrahedral configuration of the phosphonate linkage can be exploited to optimize ligand-receptor binding. See Bartlett and Marlowe (1983) *Biochemistry* 22:4618–24.

Literature examples of specific uses of peptidylphosphonates are numerous. For example, these compounds are recognized as effective transition-state analogue inhibitors for a variety of enzymes, including a number of other proteases and esterases (see, e.g., Morgan et al. (1991) *J. Am. Chem. Soc.* 113:297 and Bartlett et al. (1990) *J. Org. Chem.* 55:6268). Peptidylphosphonate esters have been used as nonhydrolyzable analogues of phosphates to inhibit dinucleoside triphosphate hydrolase (see, e.g., Blackburn et al. (1987) *Nucl. Acids Res.* 15:6991), phosphatidyltransferase (see, e.g., Vargas (1984) *Biochim. Biophys. Acta* 796:123), and squalene synthetase (see, e.g., Biller et d. (1988) *J. Med. Chem.* 31:1869). In fact, the most potent non-covalent enzyme inhibitor known is a phosphonyltripeptide inhibitor of carboxypeptidase A, which binds with 11 femptomolar (fM) $K_D$. See Kaplan et al. (1991) *Biochem.* 30:8165–8170. In addition, phosphonate esters have been used as haptens for the production of catalytic antibodies possessing esterase activity ( see, e.g., Jacobs et al. (1987) *J. Am. Chem. Soc.* 109:2174; Tramontano et al. (1986) *Science* 234:1566; and Pollack et al. (1986) *Science* 234:1570; see also, U.S. patent application Ser. No. 858,298, filed Mar. 26, 1992). Some peptidylphosphonates analogues are commercially available therapeutics. For instance, the drugs Monopril and Fosinopril are available from Bristol Myers, Squibb (Evansville, Ind.).

α-Aminophosphonates are a member of a broader class of compounds, phosphonic acid monoesters. These monoesters have typically been synthesized by one of two methods. In the first, a monomethyl alkylphosphoryl chloride is treated with an alcohol. Selective deesterification of the methyl ester yields the desired product. The monomethyl alkylphosphoryl chloride is produced by the direct action of $PCl_5$ on a phosphonate diester (see Balthazor et al. (1980) *J. Org. Chem.* 45:530) or by base hydrolysis of the phosphonate diester followed by reaction with thionyl chloride (see Bartlett et al. (1990) *J. Org. Chem.* 55:6268).

Alternatively, the direct monoesterification of a phosphonic acid can be accomplished with the appropriate alcohol and condensing reagents (see Gilmore et al. (1974,) *J. Pharm. Sci.* 63:965), such as 1,3-dicyclohexylcarbodiimide (DCC) or trichloroacetonitrile (see, e.g., Wasielewski et al. (1976) *J. Rocz. Chem.* 50:1613). A large excess of both the condensing agent and alcohol is required, and yields vary depending on the components being coupled. In addition, forcing conditions are required, such as heating to reflux temperature in a solution of THF with triethylamine and DCC, and to 50° C.–80° C. in pyridine with trichloroacetonitrile, conditions that can lead to decomposition of starting material. In addition, product yields are extremely sensitive to steric encumbrance from the reacting components, and in some cases, no product formation is observed.

The Mitsunobu reaction is a mild and effective method utilizing the redox chemistry of triphenylphosphine and a dialkylazodicarboxylate to condense an acidic reagent with primary and secondary alcohols (see Mitsunobu, (1981) *Synthesis* 1–28). Mitsunobu does not describe the reaction of phosphate esters with secondary or tertiary alcohols or the reaction of phosphonates with alcohols. The Mitsunobu reaction has been used with carboxylic acids, phenols, and phosphates as the acidic component, but only one example using a phosphonic acid has been described.

In this example (see Norbeck et al. (1987) *J. Org. Chem.* 52:2174), a monomethyl phosphonate and a primary alcohol were reacted under modified Mitsunobu conditions (triphenylphosphine and diisopropylazodicarboxylate) to produce a phosphonate diester. Demethylation using triethylamine and thiophenol produced the phosphonate monoester. Yields, however, were low for the condensation of a phosphate monoester with even a primary alcohol. Only moderate yields were obtained with elevated temperatures or with hexamethylphosphorous triamide (HMPT) as the solvent.

Recently, innovative combinatorial strategies for synthesizing large numbers of polymeric compounds on solid supports have been developed. One such method, referred to as VLSIPS ™ ("Very Large Scale Immobilized Polymer Synthesis"), is described in U.S. patent application Ser. No. 07/805,727, filed Dec. 6, 1991, which is a continuation-in-part of Ser. No. 07/624,120, filed Dec. 6, 1990, which is a continuation-in-part of U.S. Pat. No. 5,143,854, which is a continuation-in-part of Ser. No. 07/362,901, filed Jun. 7, 1989, and now abandoned. Such techniques are also described in PCT publication No. 92/10092. Related combinatorial techniques for synthesizing polymers on solid supports are discussed in U.S. patent application Ser. No. 07/946,239 filed Sep. 16, 1992which is a continuation-in-part of Ser. No. 07/762,522 filed Sep. 18, 1991 and U.S. patent application Ser. No. 07/980,523 filed Nov. 20, 1992 which is a continuation-in-part of Ser. No. 07/796,243 filed Nov. 22, 1991. Briefly, a combinatorial synthesis strategy is an ordered strategy for parallel synthesis of diverse polymer sequences by sequential addition of reagents to a solid support.

To synthesize phosphonates, and particularly peptidylphosphonates, on a solid support, one needs a general method for introducing the phosphonic acid monoester functionality. However, the phosphonate synthesis procedures described above generally have not proved easily modified for solid phase applications, which presents a significant problem for the medicinal chemist. Thus, there remains a need for chemical synthesis methods for use in the VLSIPS ™ method to generate and screen large numbers of peptidylphosphonates and other compounds containing phosphonate ester building blocks. This method should be compatible with a variety of functional groups and consistently produces high yields of the desired compounds and that can be applied to solution as well as solid phase chemistry. The present invention meets these needs.

SUMMARY OF THE INVENTION

The present invention provides methods for producing phosphonate esters. In one embodiment, the present invention relates to a method for synthesizing a phosphonic acid monoester from a phosphonate with a structure:

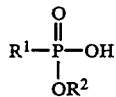

wherein $R^1$ is selected from the group consisting of alkyl, aryl, substituted alkyl, substituted aryl, heteroaryl, alkylaryl, and aminoalkyl, and $R^2$ is selected from the group consisting of methyl, ethyl, benzyl, and substituted benzyl, by treating said phosphonate with a dialkylazodicarboxylate, a triarylphosphine, and a primary or secondary alcohol with a structure $R^3OH$, wherein $R^3$ is selected from the group consisting of alkyl, aryl, substituted alkyl, substituted aryl, and aminoalkyl and wherein said alcohol is present in excess, said excess being greater than a ratio of 1.1 equivalents of alcohol to one equivalent of phosphonate, in an aprotic solvent to yield a phosphonate diester with a structure:

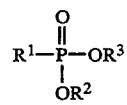

wherein $R^2$ and $R^3$ are not identical, and $R^2$ can be selectively hydrolyzed without hydrolyzing $R^3$, and treating said phosphonate diester to hydrolyze selectively said phosphonate diester to yield said phosphonic acid monoester with a structure:

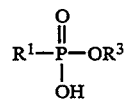

In a preferred embodiment, $R^2$ is methyl, said dialkylazodicarboxylate is diisopropylazodicarboxylate (DIAD), said triarylphosphine is triphenylphosphine (TPP), said solvent is tetrahydrofuran (THF), and trimethylsilyl bromide (TMSBr) is added directly to the reaction mixture after completion of esterification to effect selective hydrolysis of the methyl ester to yield the desired phosphonic acid monoester.

In another preferred embodiment, the present invention relates to a method for synthesizing a phosphonic acid monoester from a phosphonate with a structure:

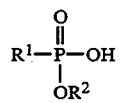

wherein $R^1$ is selected from the group consisting of alkyl, aryl, substituted alkyl, substituted aryl, heteroaryl, alkylaryl, and aminoalkyl, and $R^2$ is selected from the group consisting of methyl, ethyl, benzyl, and substituted benzyl, by:

treating said phosphonate with a dialkylazodicarboxylate, and a triarylphosphine, wherein at least one of the aryl groups of the triarylphosphine bears an electron withdrawing substituent;

treating this mixture with a primary or secondary alcohol with a structure $R^3OH$, wherein $R^3$ is selected from the group consisting of alkyl, aryl, substituted alkyl, substituted aryl, and aminoalkyl and wherein said phosphonate is present in excess, said excess being greater than a ratio of 1.1 equivalents of phosphonate to one equivalent of alcohol, and an exogenous base, in an aprotic solvent to yield a phosphonate diester with a structure:

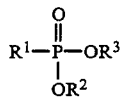

wherein $R^2$ and $R^3$ are not identical, and $R^2$ can be selectively hydrolyzed without hydrolyzing $R^3$, and then treating said phosphonate diester to hydrolyze selectively said phosphonate diester to yield said phosphonic acid monoester with a structure:

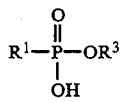

In a preferred embodiment, $R^2$ is methyl, said dialkylazodicarboxylate is diisopropylazodicarboxylate (DIAD), said triarylphosphine is tris(4-chlorotriphenyl)phosphine (CTPP), said base is diisopropylethylamine (DIEA), said solvent is tetrahydrofuran (THF), and trimethylsilyl bromide (TMSBr) is added directly to the reaction mixture after completion of esterification to effect selective hydrolysis of the methyl ester to yield the desired phosphonic acid monoester.

In yet another preferred embodiment, the phosphonate is an α-aminoalkylphosphonate, because the resulting compound is an amino acid analogue particularly useful in the production of compounds that can be screened for pharmacological activity or used in the generation of catalytic antibodies. In addition, this preferred embodiment of the reaction can be carried out on a solid support to which is covalently linked the hydroxyl group of the alcohol moiety. The solid support can be a glass slide or other suitable substrate for light directed and other combinatorial synthesis strategies described below. In this embodiment, the invention also provides novel hydroxyacid and phosphonate ester building blocks protected with photoremovable protecting groups and methods for their production. The solid support can also be beads or particles, which are preferred for use in other combinatorial synthesis strategies.

Thus, in an especially preferred embodiment of this aspect of the invention, the solid support comprises an amine group of an amino acid or peptide, and the support is treated so as to couple a hydroxy acid to said amine group to yield a hydroxyl moiety covalently linked to said support. The support is then treated with:

an α-aminoalkylphosphonate with the following structure:

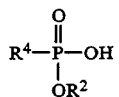

wherein $R^4$ is an α-aminoalkyl group, and $R^2$ is selected from the group consisting of methyl, ethyl, benzyl, and substituted benzyl;
a dialkylazodicarboxylate;
an exogenous base, such as DIEA; and
a triarylphosphine, such as CTPP or TPP,
to couple said α-aminoalkylphosphonate to said hydroxyl groups on said surface. In a preferred embodiment, a triarylphosphine wherein at least one of the aryl groups of the triarylphosphine bears an electron withdrawing substituent. This process can be continued by selective hydrolysis of the $R^2$ group (e.g., by treatment with TMSBr or triethylammonium phenoxide) and/or by further couplings to the amine group of said α-aminoalkylphosphonate.

The invention further provides a method of forming an array of phosphonate esters or phosphonic acids. These defined arrays or libraries of oligonucleotide will find a variety of uses, for example, to screen the substrate-bound compounds for biological activity.

In another embodiment, the invention provides a method for producing symmetric phosphonate diesters. In this embodiment, a phosphonic acid with a structure:

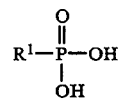

wherein $R^1$ is selected from the group consisting of alkyl, aryl, substituted alkyl, substituted aryl, heteroaryl, alkylaryl, and aminoalkyl, is treated with a dialkylazodicarboxylate, a triarylphosphine, and a primary or secondary alcohol with a structure $R^3OH$, wherein $R^3$ is selected from the group consisting of alkyl, aryl, substituted alkyl, substituted aryl, and aminoalkyl, dissolved in solvent to yield a phosphonate diester with a structure:

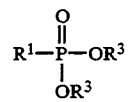

In a preferred embodiment, said dialkylazodicarboxylate is DIAD, said triarylphosphine is TPP, and said solvent is THF. In a preferred embodiment for use with secondary alcohols, the alcohol is either present in excess, or the alcohol, dialkylazodicarboxylate, and triphenylphosphine are allowed to react to form an alkoxyphosphorane before the addition of the phosphonic acid to the reaction mixture.

A further understanding of the nature and advantages of the inventions herein may be realized by reference to the remaining portions of the specification and the attached drawings.

DESCRIPTION OF THE SPECIFIC EMBODIMENTS

I. Terminology

Figure 1:
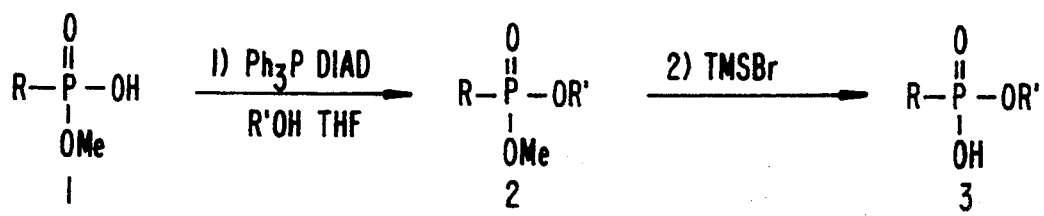
FIG. 1 shows the reaction in which a methyl phosphonate (compound 1) is coupled to an alcohol to yield the ester (compound 2), which is then treated with TMSBr to effect selective hydrolysis of the methyl ester and yield the desired phosphonic acid monoester (compound 3).

Unless otherwise stated, the following terms used in the specification and claims have the meanings given below:

"Alkyl" refers to a cyclic, branched, or straight chain chemical group containing only carbon and hydrogen, such as methyl, heptyl, —$(CH_2)_2$—, and adamantyl. Alkyl groups can either be unsubstituted or substituted with one or more substituents, e.g., halogen, alkoxy, acyloxy, amino, hydroxyl, mercapto, carboxy, benzyloxy, phenyl, benzyl, or other functionality which may be suitably blocked, if necessary for purposes of the invention, with a protecting group. Typically, alkyl groups will comprise 1 to 12 carbon atoms, preferably 1 to 10, and more preferably 1 to 8 carbon atoms.

An "α-amino acid" consists of a carbon atom, called the α-carbon, to which is bonded an amino group and a carboxyl group. Typically, this α-carbon atom is also bonded to a hydrogen atom and a distinctive group referred to as a "side chain." The hydrogen atom may also be replaced with a group such as alkyl, substituted alkyl, aryl, substituted aryl, heteroaryl, and other groups. The side chain of the amino acid is designated as group $R^1$ in FIG. 3. The side chains of naturally occurring amino acids are well known in the art and include, for example, hydrogen (as in glycine), alkyl (as in alanine (methyl), valine (isopropyl), leucine (sec-butyl), isoleucine (iso-butyl), and proline (—$(CH_2)_3$—)), substituted alkyl (as in serine (hydroxymethyl), cysteine (thiomethyl), aspartic acid (carboxymethyl), asparagine, arginine, glutamine, glutamic acid, and lysine), arylalkyl (as in phenylalanine, histidine, and tryptophan), substituted arylalkyl (as in tyrosine and thyroxine), and heteroaryl (as in histidine). See, e.g., Harper et al. (1977) Review of Physiological Chemistry, 16th Ed., Lange Medical Publications, pp. 21–24.

In addition to naturally occurring side chains, the amino acids used in the present invention may possess synthetic side chains. A "synthetic side chain" is any side chain not found in a naturally occurring amino acid. For example, a synthetic side chain can be an isostere of the side chain of a naturally occurring amino acid. Naturally occurring and synthetic side chains may contain reactive functionalities, such as hydroxyl, mercapto, and carboxy groups. One skilled in the art will appreciate that these groups may have to be protected to carry out the desired reaction scheme. As stated above, the hydrogen at the α-carbon can also be replaced with other groups; those of skill in the art recognize the medicinal importance of α-methyl amino acids and other α-, α-disubstituted amino acids.

"Aminoalkyl" refer to the group —$C(NR'R'')R^1R^2$,- where $R^1$, $R^2$, $R'$ and $R''$ are independently selected from the group consisting of hydrogen, alkyl, and aryl. Preferably, the amino alkyl group will be derived from an alpha-amino acid HOOC—$C(NR'R'')R^1R^2$ where $R^1$ and $R^2$ are the side chains of the amino acid.

"Aryl" or "Ar" refers to a monovalent unsaturated aromatic carbocyclic group having a single-ring (e.g., phenyl) or multiple condensed rings (e.g., naphthyl or anthryl), which can optionally be unsubstituted or substituted with amino, hydroxyl, lower alkyl, alkoxy, chloro, halo, mercapto, and other substituents. Preferred aryl groups include phenyl, 1-naphthyl, and 2-naphthyl.

"Arylalkyl" refers to the groups R-Ar and R-HetAr, where Ar is an aryl group, HetAr is a heteroaryl group, and R is straight-chain or branched-chain aliphatic group. Examples of arylalkyl groups include benzyl and furfuryl.

"Electron withdrawing group" refers to a substituent that draws electrons to itself more than a hydrogen atom would if it occupied the same position in a molecule. Examples of electron withdrawing groups include —$NR_3+$, —COOH, —OR, —$SR_2+$, —F, —COR, —Cl, —SH, —$NO_2$, —Br, —SR, —$SO_2R$, —I, —OH, —CN, —C≡CR, —COOR, —Ar, —CH=$CR_2$, where R is alkyl, aryl, arylalkyl, or heteroaryl.

"Exogenous base" refers to nonnucleophilic bases such as alkali metal acetates, alkali metal carbonates, alkaline metal carbonates, alkali metal bicarbonates, tri(lower alkyl) amines, and the like, for example, sodium acetate, potassium bicarbonate, calcium carbonate, diisopropylethylamine, triethylamine, and the like.

"Heteroaryl" or "HetAr" refers to a monovalent unsaturated aromatic carbocyclic group having a single ring (e.g., pyridyl or furyl) or multiple condensed rings (e.g., indolizinyl or benzothienyl) and having at least one hetero atom, such as N, O, or S, within the ring, which can optionally be unsubstituted or substituted with amino, hydroxyl, alkyl, alkoxy, halo, mercapto, and other substituents.

"Limiting reagent" refers to that substance which limits the maximum amount of product formed in a chemical reaction, no matter how much of the other reactants remains.

"Lower alkyl" refers to an alkyl group of one to six carbon atoms. Lower alkyl groups include those exemplified by methyl, ethyl, n-propyl, i-propyl, n-butyl, t-butyl, i-butyl (2-methylpropyl), cyclopropylmethyl, i-amyl, n-amyl, and hexyl. Preferred lower alkyls are methyl and ethyl. If more than one alkyl group is present in a given molecule, then each may be independently selected from "lower alkyl" unless otherwise stated.

"Phosphonate ester," "alkylphosphonate ester," "alkylphosphonic acid ester," or "phosphonic acid ester" refers to the group (RPO)(OR')(OR") where R, R' and R" are independently selected from the group consisting of hydrogen, alkyl, substituted alkyl, aryl, substituted aryl, arylalkyl, and heteroaryl, provided both R' and R" are not hydrogen, in which case the group is a phosphonic acid. "Phosphonate monoester," "alkylphosphonate monoester," "alkylphosphonic acid monoester", or "phosphonic acid monoester" refers to a phosphonate ester where R' is hydrogen and R" is alkyl, substituted alkyl, aryl, substituted aryl, arylalkyl, or heteroaryl. With respect to nomenclature, note that compound 1 in FIG. 1, if R is N-benzyloxycarbonylaminomethyl, is named methyl N-(benzyloxycarbonyl)aminomethylphosphonate.

"Phosphonic acid" or "alkylphosphonic acid" refers to the group $(RPO)(OH)_2$.

"Protecting group" refers to a chemical group that exhibits the following characteristics: (1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) generated in such projected reactions. Examples of protecting groups can be found in Greene et al. (1991) *Protective Groups in Organic Synthesis*, 2nd Ed. (John Wiley & Sons, Inc., New York). Preferred terminal amino protecting groups include benzyloxycarbonyl (CBz), 9-fluorenylmethyloxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzyl, 5-bromo-7-nitroindolinyl, and the like. Preferred hydroxyl protecting groups include Fmoc, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxymethyloxy).

"Stereospecific reaction" refers to a reaction in which bonds are broken and made at a single asymmetric atom (usually, but not necessarily carbon), and which lead largely to a single stereoisomer. If the configuration of the asymmetric carbon is altered in the process, the reaction is said to involve an inversion of configuration. If the configuration of the asymmetric carbon remains the same, the transformation occurs with retention of configuration. Stereospecific reaction sequences can be characterized as having a high percent asymmetric synthesis or percent enantiomeric excess where these terms serve as a measure of the extent to which one enantiomer is produced in excess over the other. (For example, a reaction sequence that produces 59% of one isomer and 41% of another isomer would have a percent asymmetric synthesis or percent enantiomeric excess of 59−41%=18%). Typically, the reaction sequences described herein will exhibit at least about a 50% percent enantiomeric excess; preferably, at least about a 60% percent enantiomeric excess; more preferably, at least about a 70% percent enantiomeric excess; and even more preferably, at least about an 80% percent enantiomeric excess, where a perfectly stereospecific reaction sequence would have a 100% percent enantiomeric excess. See, e.g., Morrison and Mosher, "Asymmetric Organic Reactions", 2nd Ed., American Chemical Society, Washington, D.C. (1976), which is incorporated herein by reference.

"Weak acid" refers to a substance having a $pK_a$ between about 3 and 8, and preferably between about 3 and 5. Preferred weak acids include acetic acid, citric acid, ascorbic acid, lactic acid, and the like.

II. Synthesis of Monoalkyl Phosphonates

A. The Starting Materials

1. The Phosphonate Monoester

Figure 2:
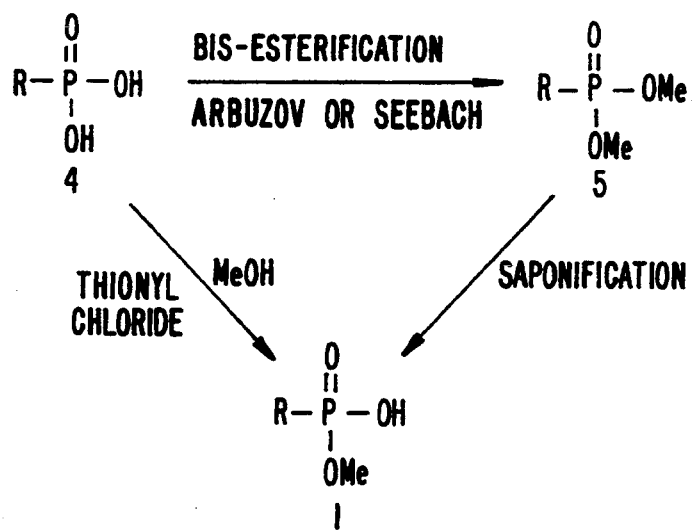
FIG. 2 shows the reaction for producing methyl phosphonates (compound 1) from either phosphonic acids (compound 4) or dimethyl phosphonates (compound 5).

Monomethyl phosphonates (compound 1, FIG. 1) are preferred for purposes of the present invention and can be readily obtained by the general procedures schematically outlined in FIG. 2. The R group of such compounds can be alkyl, aryl, heteroaryl, or arylalkyl, each of which may be optionally substituted. Some phosphonic acids (compound 4, FIG. 2) are commercially available, and for base sensitive compounds, a phosphonic acid can be mono-esterified directly to produce the monomethyl phosphonates. This esterification can be accomplished by treating a phosphonic acid with methanol and a small excess of thionyl chloride, as described by Hoffman (1986) *Synthesis*, at page 557 et seq. In addition, saponification of dimethyl phosphonates (compound 5, FIG. 2) can be used to produce the mono-methyl phosphonates in high yields. Dimethyl phosphonates can be produced either by the bis-esterification of phosphonic acids or obtained directly by the methodology of Arbuzov (see Arbuzov (1964) *Pure Appl. Chem.* 9:307) or Seebach (see Seebach et al. (1989) *Helv. Chim. Acta* 72:401).

Again with reference to FIG. 1, the methyl group of compound 1 may optionally be replaced with an ethyl, benzyl, or substituted benzyl group, or any group that can be selectively hydrolyzed from compound 2 (with the methyl group replaced by the group that substitutes for the methyl group) to yield compound 3.

2. The Alcohol

A wide variety of alcohols may be used to produce the phosphonate monoesters by the methods of the present invention. The alcohol may be primary or secondary. The R' group in the alcohol and in compounds 2 and 3 (FIG. 1) originates from the alcohol and may be alkyl, substituted alkyl, aryl, substituted aryl, arylalkyl, or heteroaryl, each of which may be optionally substituted.

With sterically undemanding alcohols, such as ethanol and isopropanol, the reaction occurs instantly, regardless of the substitutents on the phosphonate. With more sterically hindered alcohols, such as methyl mandelate, the reaction may require up to two hours to go to completion.

B. The Phosphonate as the Limiting Reagent

1. Overview

The present invention provides methods for producing phosphonate esters. In one embodiment, the present invention relates to a method for synthesizing a phosphonic acid monoester from a monoalkyl or monoaryl phosphonate, wherein the phosphonate is the limiting reagent, by treatment with a dialkylazodicarboxylate, preferably diisopropylazodicarboxylate (DIAD), a triarylphosphine, preferably triphenylphosphine (TPP), and an alcohol dissolved in a solvent, such as tetrahydrofuran (THF). In a preferred embodiment, approximately equimolar amounts of the alcohol, triarylphosphine, and dialkylazodicarboxylate are used. Typically, the ratio of phosphonate to alcohol will range from about 1:1.1 to about 1:5, preferably from about 1:1.1 to about 1:3, and more preferably about 1:1.5.

The coupling reaction proceeds stereospecifically with inversion of the stereochemistry at the carbon bonded to the hydroxyl group of the alcohol reactant. Accordingly, if the alcohol reactant has an R configuration at the carbon bonded to the hydroxyl group, the resulting phosphonate has an S configuration at the corresponding carbon.

When the coupling reaction is complete, the selective cleavage of the ester is carried out; preferably, trimethylsilyl bromide (TMSBr) is added to the reaction mixture to effect selective hydrolysis of the methyl ester and yield the desired compound (compound 3, FIG. 1). Other methods for cleaving the phosphonic acid ester can also be used; for instance, the protocols for cleaving esters of carboxylic acids described in Greene, supra, at page 156 et seq., can be used for this purpose, provided the desired selectivity of hydrolysis can be achieved.

Although FIG. 1 exemplifies the reaction as an intermolecular reaction, one of skill in the art will appreciate that the reaction may also be performed intramolecularly (i.e., the alcohol and the monomethyl phosphonate are parts of the same molecule). This embodiment allows for the synthesis of cyclic and sterically restricted phosphonates.

2. The General Procedure

The general procedure for the reaction wherein the phosphonate is the limiting reagent is as follows. To a solution of a phosphonate (compound 1, FIG. 1, 0.5 mmol), alcohol (0.75 mmol), and a triarylphosphine (0.75 mmol) in anhydrous THF (5 mL, refluxed over potassium and distilled prior to use), is added a dialkylazodicarboxylate, preferably diisopropylazodicarboxylate (0.75 mmol). Upon completion of the condensation reaction (generally, 0.5-5 hours), TMSBr (1.5 mmol) is added. The reaction is stirred for about an additional hour. The reaction mixture is then diluted with ether (10 mL) and extracted with 5% $NaHCO_3$ (twice, 10 mL each extraction). The aqueous phase is washed with ether (three times, 10 mL each wash), acidified to pH=2 with concentrated HCl, and then extracted with ethyl acetate (EtOAc, three times, 10 mL each extraction). The EtOAC)Ac phase is dried over $MgSO_4$, filtered, and concentrated to yield the desired compound. See Example 1 below.

3. The Mechanism

Figure 3:
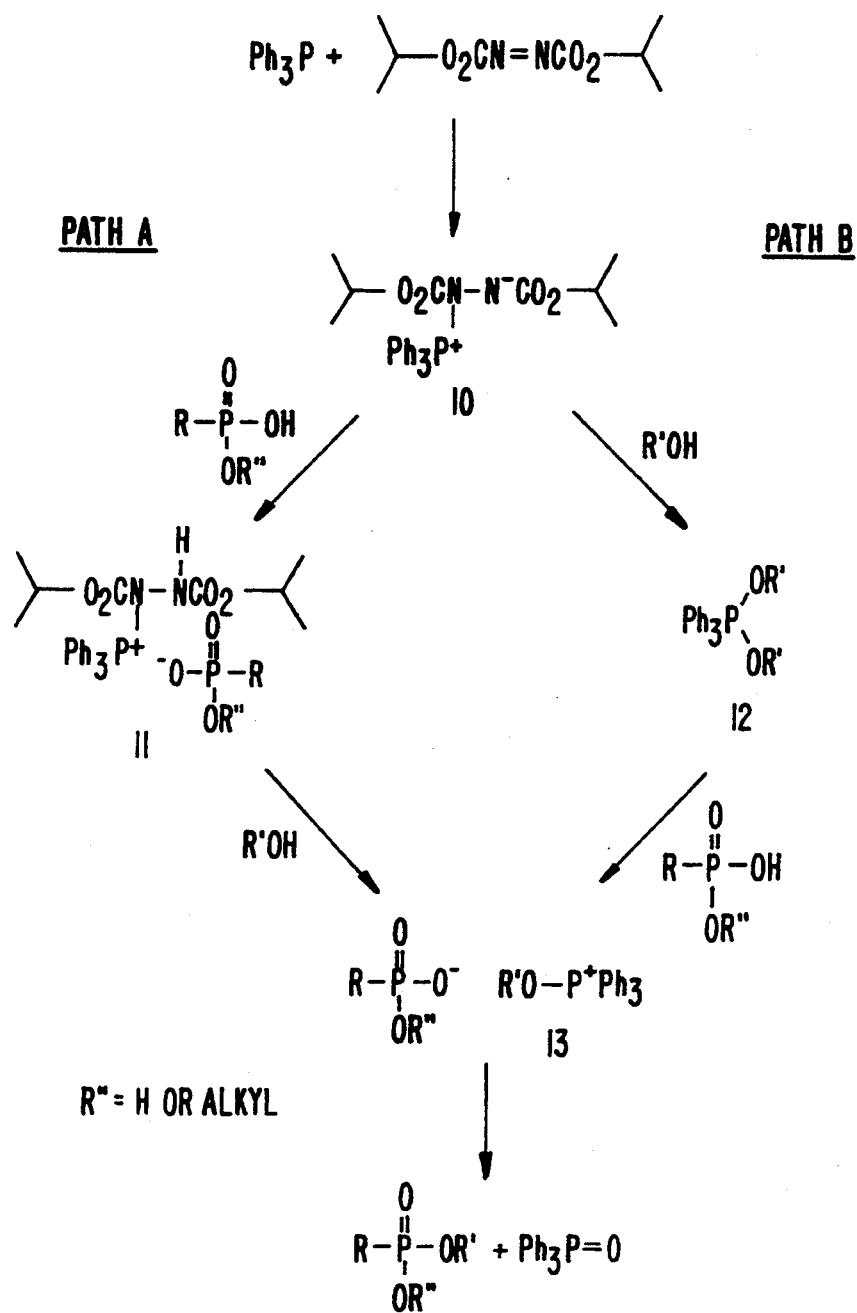
FIG. 3 shows a theoretical reaction mechanism for a method of the invention.

For a more complete understanding of the invention, one may find helpful the theoretical mechanism of the reaction. This theoretical reaction mechanism is illustrated in FIG. 3 (see also, for a discussion of the reaction mechanism for carboxylic acids, Hughes et al., (1988) *J. Am. Chem. Soc.* 21:6487; Grochowski et al., (1982) *J. Am. Chem. Soc.* 104:6876; Crich et at., (1989) *J. Org. Chem.* 54:257; and Varasi et al., (1987) *J. Org. Chem.* 52:4235).

In Path A, the betaine (compound 10) formed between triphenylphosphine and DIAD is protonated by an acidic component with pKa<11 (see Kim and Rapoport (1990) *J. Org. Chem.* 55:3699), yielding the protonated betaine (compound 11, FIG. 3), which in turn reacts with an alcohol to form the alkoxyphosphonium salt (compound 13, FIG. 3). Subsequent $S_N2$ attack by the conjugate base of compound 13 yields the esterified product with inversion of configuration at the carbinol carbon.

Path B only occurs when the acidic component is not present to protonate the betaine (compound 10, FIG. 3). Two equivalents of alcohol react with compound 10 to form a dialkoxyphosphorane (compound 12, FIG. 3; see Camp and Jenkins (1989) *J. Org. Chem.* 54:3045; Von Itzstein and Jenkins (1983) *Aust. J. Chem.* 36:557; and Guthrie and Jenkins (1982) *Aust. J. Chem.* 35:767). Upon addition of the acidic component, compound 12 is converted to the phosphonium salt (compound 13, FIG. 3), followed by product formation as in Path A. Some investigators have suggested that compound 12 (FIG. 3) is in equilibrium with an (acyloxy)alkoxyphosphorane, but whether such a compound plays a significant role in product formation is unknown (see Camp and Jenkins (1989) *J. Org. Chem.* 54:3049).

Pyrophosphonate esters presumably arise from condensation of one molecule of an alkylphosphonic acid with an electrophilic phosphorus species formed via the protonated betaine (compound 11, FIG. 3), followed by further esterification with excess alcohol. The electrophilic species derived from benzylphosphonic acid was trapped with t-butanol, yielding t-butyl benzylphosphonate. Because Mitsunobu condensations are not normally observed with tertiary alcohols (see Camp and Jenkins, supra), and no reaction with t-butanol was observed with benzylpyrophosphonate, or when methyl benzylphosphonate (this compound, as well as methyl t-butylphosphonate were obtained by treatment of the respective alkylphosphonic acids (Aldrich Chemical Co.) with diazomethane, followed by saponification) was substituted for benzylphosphonic acid, any t-butyl ester that is formed must result from nucleophilic attack by the alcohol on the electrophilic phosphorus species. The availability of this additional pathway with phosphonic acids may result in a different stereochemical configuration of the alcohol component than the normally observed inverted carbinol carbon.

To circumvent formation of the electrophilic phosphorus species, one can access Path B (FIG. 3), using reaction conditions similar to those described by Loibner and Zbiral (1976) *Helv. Chim. Acta.* 59:2100. More specifically, the alcohol, triarylphosphine, and DIAD are initially combined to produce the alkoxyphosphorane (compound 12, FIG. 3) before adding the acidic component. Formation of compound 12 prevents the acidic component from reacting with the betaine (compound 10, FIG. 3) to form the protonated betaine (compound 11, FIG. 3) and eliminates pyrophosphonate formation. Formation of compound 12 (FIG. 3) was inferred by the significant upfield shifts in the $^1$H-NMR spectrum of the alcohol protons upon addition of DIAD and triphenylphosphine.

In the slower reactions, the protonated betaine (compound 11, FIG. 3) was formed rapidly, as evidenced by an upfield shift of the phosphonic acid monoester's methylene and methoxide $^1$H-resonances, and the appearance of a proton attributable to the protonated carbamate amine in compound 11 (FIG. 3). The protonated betaine is believed then to react slowly with the alcohol to yield the desired product and diisopropylhydrazodiformate (DIHD).

4. Results

The present method has broad applicability, as shown by Table 1, below. Table 1 shows that the present method has been successfully applied to t-butyl and benzylphosphonic esters and to the synthesis of phosphorus containing peptide analogues.

TABLE 1

Alkylphosphonic acid monoester synthesis via condensations of methyl alkylphosphonates with alcohols followed by TMSBr treatment

| Phosphonate | Alcohol | Time (hr) | Yield |
|---|---|---|---|
| Methyl benzyl-phosphonate | Ethanol | 0.5 | 94% |
| | Isopropanol | 0.5 | 91% |
| | Methyl 3-L-phenyl-lactate | 1 | 80% |
| | Methyl S-mandelate | 2 | 81% |
| Methyl t-butyl-phosphonate | Ethanol | 0.5 | 81% |
| | Isopropanol | 0.5 | 88% |
| | Methyl 3-L-phenyl-lactate | 2 | 82% |
| Methyl N-CBz-amino-methylphosphonate | Methyl glycolate | 0.5 | 86% |
| | Methyl 3-L-phenyl-lactate | 1 | 78% |
| | Methyl 2-L-hydroxy-isovalerate | 3.5 | 76% |
| Methyl N-CBz-valinyl-phosphonate | Methyl glycolate | 0.5 | 83% |
| | Methyl 3-L-phenyl-lactate | 1 | 64% |
| | Methyl 2-L-hydroxy-isovalerate | 4 | 69% |

The phosphorus analogues of glycine and valine were used to observe the substituent effects of the phosphorus component on coupling rates and yields. These compounds were synthesized from the CBZ-protected amino acids by the methods of Seebach et al., supra, and Corcoran and Green (1990) *Tetr. Lett.* 31:6827. Likewise, the hydroxy analogues of glycine, phenylalanine, and valine were used to examine the scope of the method. α-L-Hydroxyisovaleric acid was purchased from Bachem Bioscience, Inc. Based on the results of previous workers comparing coupling rates for $N^\alpha$-benzyloxycarbonylamino acid p-nitrophenyl ester derivatives with amino acid esters (see Kovacs, *The Peptides: Analysis, Synthesis, Biology*, vol. 2 (Academic Press, N.Y. 1979), pp. 485–539), one might expect that the rate of phosphonate ester formation in the reaction would be sensitive to steric effects at both the alcohol and phosphorus centers. Upon comparing the reaction times required to achieve greater than 99% coupling yields (estimated by $^1$H-NMR for the phosphonic acid couplings), one surprisingly finds, however, that the reaction rate is relatively insensitive to the steric bulk of the phosphoryl residue side chain. The phosphorus Gly and Val analogues had similar reaction times, unlike the active ester condensations, which exhibited 16–22 fold differences. This tendency has been mentioned previously with regard to the coupling of amino-carboxylic acids and azido compounds via triarylphosphines. See Wilt et al., (1985) *J. Org. Chem.* 50:2601. The influence of steric effects from the hydroxy component on the reaction rate was comparable to that seen in the active ester condensations.

The following compounds have been prepared using this general method, wherein the phosphonate was the limiting reagent: ethyl benzylphosphonate, isopropyl benzylphosphonate, methyl (D)-2-O-benzylphosphoryl-3-phenylpropionate, methyl (D)-2-O-benzylphosphoryl-2-phenylacetate, ethyl t-butylphosphonate, isopropyl t-butylphosphonate, methyl (D)-2-O-t-butylphosphoryl-3-phenylpropionate, methyl 2-O-(1-N-(benzyloxycarbonyl)aminomethylphosphoryl)acetate, methyl (D)-2-O-(1-(N-(benzyloxycarbonyl)amino)methylphosphoryl)-3-phenylpropionate, methyl (D)-2-O-(1-(N-(benzyloxycarbonyl)amino)methylphosphoryl)-3-m ethylbutyrate, methyl 2-O-((R,S)-1-(N-(benzyloxycarbonyl)amino)-2-methylpropylphos phory)acetate, methyl (D)-2-O-((R,S)-1-(N-(benzyloxycarbonyl)amino)-2-methylpropylphosphoryl)-3-phenylpropionate, and methyl (D)-2-O-((R,S)-1-(N-(benzyloxycarbonyl)amino)-2-methylpropyl phosphoryl)-3-methylbutyrate.

B. The Alcohol as the Limiting Reagent

1. Overview

Thus far, discussion has focused on a general methodology for the synthesis of phosphonate esters wherein the phosphonate formed the limiting reagent. Initial attempts at modifying this reaction such that the alcohol was the limiting reagent resulted in increased reaction time and decreased yield. Surprisingly, the addition of an exogenous base and a triarylphosphine that was more electronegative at phosphorus than triphenylphosphine overcame these deficiencies.

According to this embodiment, the methyl phosphonate is treated with a dialkylazodicarboxylate, preferably DEAD or DIAD, and a triarylphosphine, wherein at least one of the aryl groups bears an electron withdrawing substituent. Typically, the electron withdrawing substituent will have a Hammett constant (s) from between about 0.05 to about 0.8, and preferably between about 0.25 to about 0.5. See Lowry and Richardson, *Mechanism and Theory of Organic Chemistry*, 2nd Ed., p. 131 (1981), and Hughes et al. (1988) *J. Am. Chem. Soc.* 110:6487, which are hereby incorporated by reference. Preferably, the phosphorus of the triarylphosphine will not be as electron deficient as tris(pentafluorophenyl)phosphine. The reaction mixture is then treated with an exogenous base and the alcohol. In a preferred embodiment, the exogenous base will be soluble in the reaction solvent. Particularly preferred exogenous bases include tri(lower alkyl)amines, such as diisopropylethylamine (DIEA) or triethylamine (TEA).

In a preferred embodiment, approximately equimolar amounts of the triarylphosphine, dialkylazodicarboxylate, and phosphonate are used. The ratio of alcohol to phosphonate will typically range from about 1:1.1 to about 1:5, preferably from about 1:1.1 to about 1:3, and more preferably about 1:1.5. An excess of either the dialkylazodicarboxylate or the triarylphosphine (e.g., up to about 5 equivalents) can be used; however, to avoid elimination and other side reactions, excess amounts of both reagents should not be used. The exogenous base is used in excess, typically, between about 2 and 10 equivalents, preferably, between about 2 and 8 equivalents, and more preferably, about 5 equivalents, based on the amount of alcohol.

The coupling reaction proceeds stereospecifically with inversion of the stereochemistry at the carbon bonded to the hydroxyl group of the alcohol reactant. Accordingly, if the alcohol reactant has an R configuration at the carbon bonded to the hydroxyl group, the resulting phosphonate has an S configuration at the corresponding carbon.

When the coupling reaction is complete, the selective cleavage of the ester is carried out; preferably, trimethylsilyl bromide (TMSBr) is added to the reaction mixture to effect selective hydrolysis of the methyl ester and yield the desired compound (compound 3, FIG. 1). Other methods for cleaving the phosphonic acid ester can also be used; for instance, the protocols for cleaving esters of carboxylic acids described in Greene, supra, at page 156 et seq., can be used for this purpose, provided the desired selectivity of hydrolysis can be achieved.

Although FIG. 1 exemplifies the reaction as an intermolecular reaction, one of skill in the art will appreciate that the reaction may also be performed intramolecularly (i.e., the alcohol and the monomethyl phosphonate are parts of the same molecule). This embodiment allows for the synthesis of cyclic and sterically restricted phosphonates.

2. The General Reaction

To a solution of methyl alkylphosphonate (1.5 mmol), alcohol (1 mmol), and a triarylphoshine, preferably, tris(4-chlorophenyl)phosphine, (1.5 mmol) dissolved in anhydrous methylene chloride (5 ml) was added dialkylazodicarboxylate, preferably DIAD or DEAD, (1.5 mmol) and an exogenous base, such as TEA or DIEA (5 mmol). Upon completion of the reaction the reaction mixture was concentrated under vacuum and purified by flash chromatography (ethyl acetate/hexanes).

3. The Mechanism

Although not wanting to be limited to the following mechanism, it is currently believed that when an equimolar excess of phosphonic acid, triphenylphosphine, and DIAD relative to the alcohol are used (entry 2, Table 2) the protonated betaine 11 is formed and reacts sluggishly with the alcohol to form the alkoxyphosphonium salt 13. See FIG. 3. When a slight excess of unprotonated betaine 11 is present (entries 1 & 3, Table 2) it assists formation of the alkoxyphosphonium salt 13 via general base catalysis. However, with a larger excess of 11 (entry 4, Table 2) path B is accessed resulting in formation of the dialkoxyphosphorane 12 which can undergo an E2 elimination instead of cascading to product. See, also, Von Itzstein and Jenkins (1983) *Aust. J. Chem.* 36:557 and Loibner and Zbiral (1977) *Helv. Chim. Acta* 60:417.

This pathway is circumvented, at least in part, by the addition of an exogenous base as a general base catalyst which serves to increase the rate of reaction between the alcohol and 11 to form 13. Moreover, increasing the electrophilicity of phosphorus in 11 increases the rate of formation of 13. Additionally, to prevent access to path B and potential elimination reactions, an equimolar excess of phosphonic acid, phosphine, and DIAD should be used.

4. The Results

The results are summarized in Table 2 (entries 5–7). All couplings were performed with an equimolar excess of phosphonic acid, DIAD and phosphine relative to the alcohol.

TABLE 2

| Reaction Times for Phosphonic Acid Couplings | | | | | | |
|---|---|---|---|---|---|---|
| Phosphonic Acid | Alcohol | TPP | CTPP[1] | DIAD | TEA | Coupling Time[2] |
| 1.0 | 1.5 | 1.5 | — | 1.5 | — | 1 |
| 2.0 | 1.0 | 2.0 | — | 2.0 | — | >72 |
| 1.5 | 1.0 | 2.0 | — | 2.0 | — | 12 |
| 1.5 | 1.0 | 3.0 | — | 3.0 | — | —[3] |
| 2.0 | 1.0 | 2.0 | — | 2.0 | 5.0 | 8 |
| 2.0 | 1.0 | — | 2.0 | 2.0 | — | 6 |
| 2.0 | 1.0 | — | 2.0 | 2.0 | 5.0 | 0.5 |

[1] Tris(4-chlorophenyl)phosphine [2] Hours [3] Negligible product formation

Upon addition of TEA the reaction time was reduced to 8-hours (entry 5, Table 2). A number of commercially available phosphines with electron withdrawing substituents on the phenyl rings were investigated. The most electron deficient phosphine studied was tris(pentafluorophenyl)-phosphine (s=0), however it was unable to form the betaine 10 as evidenced by $^1$H-NMR. Relative to triphenylphosphine only a modest improvement in reaction time was observed with tris(4-fluorophenyl)phosphine (s=0.06) while tris(4-chlorophenyl)-phosphine (s=0.23) reduced the reaction time to 6-hours (entry 6, Table 2).

Combining the addition of an exogenous base with tris(4-chlorophenyl)phosphine substituted for TPP (entry 7, Table 2) reduced the reaction time to 0.5-hours which is comparable to the standard Mitsunobu coupling results (entry 1, Table 2). Additional improvements in rates and yields can be achievable with more electron deficient phosphines providing this doesn't result in an E2 elimination reaction of the alkoxyphosphonium salt.

The effect of additional steric encumbrance on the yields and reaction times was also studied and the results summarized in Table 3. Satisfactory results were obtained even with the most sterically demanding couplings. The coupling times, and yields are comparable to the results we previously reported for the standard Mitsunobu procedure under phosphonic acid limiting conditions. Supra. If desired, selective demethylation of the resulting unsymmetrical phosphonate diesters can be accomplished with either TMSBr (see Campbell (1992) *J. Org. Chem.* 57:6331) or triethylammonium phenoxide (see Norbeck et al. (1987) *J. Org. Chem.* 52:2174).

TABLE 3

Alkylphosphonic acid monoester synthesis via condensations of methyl alkylphosphonates with alcohols followed by TMSBr treatment

| Phosphonate | Alcohol | Time (hr) | Yield |
|---|---|---|---|
| Methyl benzyl-phosphonate | Isopropanol | 0.5 | 91% |
|  | Methyl glycolate | 0.3 | 81% |
|  | Methyl D-lactate | 0.3 | 88% |
|  | Methyl 3-D-phenyl-lactate | 0.5 | 79% |
|  | Methyl 2-D-hydroxy-isovalerate | 3.0 | 61% |
| Methyl N-CBz-amino-methylphosphonate | Methyl D-lactate | 0.5 | 81% |
|  | Methyl 3-D-phenyl-lactate | 0.5 | 72% |
|  | Methyl 2-D-hydroxy-isovalerate | 4.0 | 50% |
| Methyl (R)-[N-CBz-alanylphosphonate | Methyl D-lactate | 0.5 | 81% |
|  | Methyl 3-D-phenyl-lactate | 0.5 | 84% |
|  | Methyl 2-D-hydroxy-isovalerate | 3.5 | 43% |
| Methyl (R,S)-[N-CBz-valinyl-phosphonate | Methyl D-lactate | 0.5 | 88% |
|  | Methyl 3-D-hydroxy-phenyl lactate | 0.5 | 80% |
|  | Methyl 2-D-hydroxy-isovalerate | 7.0 | 53% |

C. α-Aminoalkylphosphonates

In another important embodiment, an aminoalkylphosphonate (compound 9, FIG. 4) serves as the phosphonate. In this embodiment, the $R^1$ and $R^2$ groups of compound 9 (FIG. 4) typically are derived from an amino acid and are independently selected from hydrogen, alkyl, heteroalkyl, aryl, arylalkyl, and heteroaryl, each of which may be optionally substituted. In addition, $R^1$, $R^2$, and the nitrogen atom to which $R^2$ is attached may form a heterocyclic ring. According to some embodiments, $R^2$ will be a protecting group.

When the phosphonate is an α-aminoalkylphosphonate in the method of the present invention, the resulting compound, e.g., a methyl α-aminoalkylphosphonate diester, is particularly useful in the production of compounds that have pharmacological activity or can be used in the generation of catalytic antibodies. In one embodiment, this aspect of the invention is directed to the synthesis of peptide analogues that possess a phosphonate linkage in the place of an amide or amidomimetic linkage in the peptide or peptidomimetic. These peptide analogues can be prepared from the corresponding aminoalkylphosphonates, as discussed below.

Figure 4:
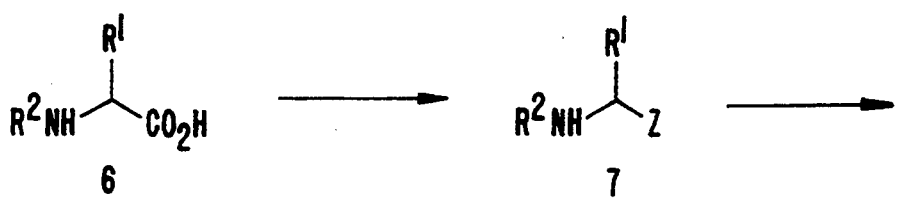
FIG. 4 shows the reaction for producing monomethyl peptidylphosphonates (compound 9) from amino acids or peptides.
Figure 4:
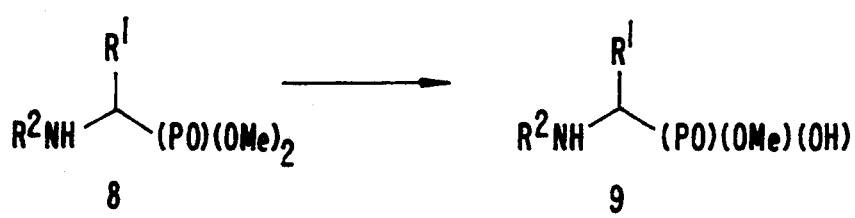

To prepare peptidylphosphonates according to the methods of the present invention, a monomethyl aminoalkylphosphonate (compound 9, FIG. 4) is first prepared. Monomethyl aminoalkylphosphonates can be produced from amino acids, as shown in FIG. 4. A variety of N-protected amino acids (compound 6, FIG. 4) can be used to prepare aminoalkylphosphonates. Although α-aminoalkylphosphonates are preferred for many purposes of the invention, the invention is equally applicable to other aminoalkylphosphonates, such as beta-amino acid phosphonate derivatives and other derivatives where the number of carbon atoms between the amino group and the phosphonate group is more than one.

To prepare compounds such as compound 7 (FIG. 4), the amino group of the amino acid (compound 6, FIG. 4) must be protected. One skilled in the art will appreciate that any one of a variety of terminal amino protecting groups may be used. The terminal amino protecting group corresponds to the group $R^2$ in compounds 6 through 9 (FIG. 4). Examples of terminal amino protecting groups may be found in Greene et al., supra, and include carbamates, amides, N-alkyl groups, N-aryl groups, etc. Preferred amino protecting groups include the carbobenzyloxy group (CBz), the 9-fluorenylmethyl carbamate group (Fmoc), and the NPEOC group.

Aminophosphonates can be produced from amino acids by decarboxylation according to the following reaction. Compound 7 (FIG. 4), where Z is acetoxy, can be prepared by the procedure of Corcoran et al. (1990) *Tetr. Lett.* 31:6827–6830. The Corcoran et al. reference describes the oxidative decarboxylation of N-protected amino acids with lead tetraacetate. Compound 7, where Z is either iodo, bromo, or chloro, can be prepared through the treatment of an N-protected amino acid (compound 6, FIG. 4) with lead tetraacetate and halide ions, preferably iodine, bromide, and chloride. This general procedure is reported in Kochi (1965) *J. Am. Chem. Soc.* 87:2500. A review of this reaction can be found in Sheldon and Kochi (1972) *Org. React.* 19:279–421. Alternatively, compound 7, where Z is either iodo, bromo, or chloro, can be prepared from an N-protected amino acid using the procedures outlined in March, 1985, *Advanced Organic Chemistry* 3rd Ed. (John Wiley & Sons, New York), pp. 654–655.

Figure 5:
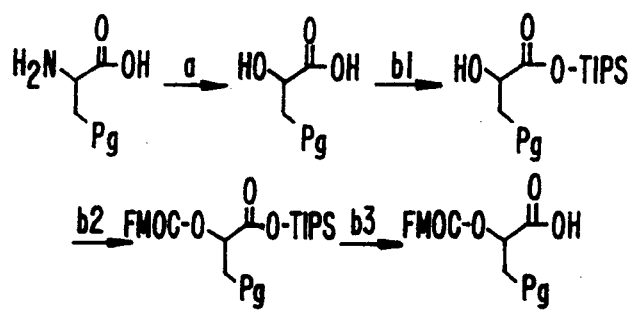
FIG. 5 illustrates the synthetic protocol for the production of side chain functionalized α-FMOC-hydroxy acids.

Compound 8 (FIG. 4) can be prepared through a variety of synthetic sequences. According to a preferred embodiment, these compounds can be produced stereospecifically using the procedure described in U.S. Pat. No. 5,362,899, which is incorporated herein by reference, and illustrated in FIG. 5. This procedure provides for the conversion of a protected amino acid to the corresponding acyl aroyl or diacyl peroxide which then spontaneously rearranges to form an alpha amino ester. The ester subsequently can be converted to an appropriate leaving group which is displaced with a phosphite to yield Compound 8.

Compound 8 also can be produced via the reaction of compound 7, where Z is acetoxy or halo, with trimethylphosphite. See Corcoran, supra; see also, Seebach, supra. A review of this general reaction can be found in Arbuzov, supra. In a preferred embodiment, compound 7 (FIG. 4), where Z is acetoxy, is treated with trimethylphosphite in the presence of titanium tetrachloride to produce compound 8.

To illustrate this aspect of the invention, one can prepare dimethyl [1-[N-(benzyloxycarbonyl)-amino]-2-methylpropyl]phosphonate (see compound 8, FIG. 4) from 1-acetoxy-1 -N-(benzyloxycarbonyl)amino-2-methylpropane (see compound 7, FIG. 4), or one can prepare dimethyl [1-[N-(benzyloxycarbonyl)-amino]-ethyl]phosphonate from 1-acetoxy-1-N-(benzyloxycarbonyl)aminoethane by dissolving the starting compound in a polar aprotic solvent, such as methylene chloride, under an inert atmosphere. Trimethylphosphite is then added, and the mixture is cooled, preferably to between 0° C. and −78° C. A dilute solution, preferably 1M, of titanium tetrachloride in a polar aprotic solvent, such as methylene chloride, is slowly added to the solution of the compound, and the reaction is stirred at room temperature until the reaction is complete. See Example 3 below.

The dimethyl phosphonates characterized by the structure of compound 8 (FIG. 4) may be saponified to yield monomethyl phosphonates (compound 9, FIG. 4) using a variety of techniques. In a preferred embodiment, the saponification is accomplished under basic conditions. To illustrate this aspect of the invention, one can prepare methyl [1-[N-(benzyloxycarbinyl)-amino]-ethyl]phosphonate (see compound 9, FIG. 4) from dimethyl [1-[N-(benzyloxycarbonyl)-amino]-ethyl]phosphonate (see compound 8, FIG. 4), or one can prepare methyl [1-[N-(benzyloxycarbonyl)-amino]-2-methylpropyl]phosphonate from dimethyl [1-[N-(benzyloxycarbonyl)-amino]-2-methylpropyl]phosphonate by dissolving the starting compound in a polar protic solvent and a strong aqueous base, preferably concentrated aqueous sodium hydroxide or concentrated aqueous lithium hydroxide, and heating the resulting mixture for a time sufficient to hydrolyze the ester group. See Example 3 below.

D. Solid State Synthesis

1. Overview

One can synthesize many pharmaceutically important compounds by the method of the present invention. As already noted, the present methods are also amenable to synthesis reactions carried out on a solid support or substrate, an important aspect of the present invention. Synthesis in this format is desirable primarily because of the ease with which one can synthesize and screen large numbers of molecules for desired properties. In addition, this synthesis format may be preferred, because byproducts, such as unreacted starting materials, solvents, deprotection agents, etc., may simply be washed away from the desired solid support-bound product.

2. Substrates

In accordance with the present invention, solid phase substrates include beads and particles, such as peptide synthesis resins (see, e.g., Merrifield (1963) *J. Am. Chem. Soc.* 85:2149–54; U.S. patent application Ser. No. 762,522, filed Sep. 18, 1991; U.S. patent application Ser. No. 876,792, filed Apr. 29, 1992; and Houghten, U.S. Pat. No. 4,631,211), rods (see, e.g., Geysen et al. (1984) *Proc. Natl. Acad. Sci.* USA 81:3998–4002, and Geysen et al., 1986, PCT patent publication No. WO 86/00991), glass slides (see Fodor et al. PCT patent publication No. WO 92/10092), and any additional support upon which peptides or other organic compounds can be synthesized. Thus, the solid substrate may be composed of any of a wide variety of materials, for example, polymers, plastics, resins, polysaccharides, silicon or silica-based materials, carbon, metals, inorganic glasses, and membranes.

The surface of the substrate is preferably provided with a layer of linker molecules, although one of skill in the art understands that the linker molecules are optional and not strictly required. The linker molecules are of sufficient length to permit compounds attached to the substrate to interact freely with molecules exposed to the substrate. The linker molecules can be 6-50 atoms long or longer to provide optimum exposure. The linker molecules, may be, for example, aryl acetylene, or ethylene glycol oligomers, or diamines, diacids, amino acids, or combinations thereof in oligomer form, each oligomer containing 2 to 10 or more monomer units. Other linker molecules may also be used.

The linker molecules can be attached to the substrate via carbon-carbon bonds using, for example, (poly)trifluorochloroethylene surfaces, or preferably, by siloxane bonds (using, for example, glass or silicon oxide surfaces). Siloxane bonds with the surface of the substrate may be formed via reactions of linker molecules bearing trichlorosilyl groups. The linker molecules may optionally be attached in an ordered array, i.e., as parts of the head groups in a polymerized Langmuir Blodgett film. In alternative embodiments, the linker molecules are adsorbed to the surface of the substrate.

On the distal or terminal end of the linker molecule opposite the substrate, the linker molecule is provided with a functional group. This functional group is used to bind a protective group, a substrate, or a reactant, depending on the format desired and the stage of synthesis. Typically, the functional group will comprise a hydroxyl group, a mercapto group, an amino group, a carboxylic acid group, a thiol group, or other groups capable of bonding to the reactant.

3. Coupling Chemistry

For a better understanding of the wide variety of solid supports, linkers, and screening methods compatible with the present invention, the following specific method for incorporating the phosphonate transition-state analog pharmacaphore into a growing peptide chain via solid phase synthesis is provided.

The solid phase synthesis of a peptidylphosphonate begins with the construction of a peptide of desired length and sequence using standard FMOC peptide synthesis methodology. Incorporation of a phosphonate linkage requires two unnatural (non-peptidyl) building blocks: (1) an appropriately protected aminophosphonic acid; and (2) an appropriately protected alpha-hydroxy acid (for example, an analog of a genetically coded α-amino acid).

Secondary alcohols, such as the side chain hydroxyl of threonine, have been shown to be unreactive toward modern amino acid coupling agents, such as BOP and HBTu. Surprisingly, however, most of the secondary hydroxyls of the alpha-hydroxy acids are reactive toward these agents, at least in the present methods, and therefore must be suitably protected during coupling to an amino acid. The reaction is schematically outlined in FIG. 6.

Chemical peptide synthesis typically proceeds in the carboxy-to-amino (C to N) direction. Incorporation of the phosphonate proceeds in two steps. First, a suitable protected hydroxy acid, typically, an alpha-O-FMOC-hydroxy acid or an alpha-O-NPEOM-hydroxy acid, is attached to the peptide's amino-terminus using standard peptide coupling conditions, in the example shown, HBTu (2-(1H-benzotriazol-1-yl)-1,1,3,3-tetramethyluronium hexafluorophosphate) chemistry. The hydroxyl protecting group is removed. Treatment with 30% piperidine or 5% DBU in NMP removes the FMOC group and the yields for the coupling of the hydroxy acid to the substrate can be assessed by UV analysis using the fluorene chromophore of the dibenzofulvene-piperidine adduct (301 nm, $\epsilon = 7800$ M$^{-1}$ cm$^{-1}$, see Bernatowicz et al. (1989) Tetrahedron Lett. 30:4645).

Synthesis of the peptidylphosphonate proceeds by coupling the resin bound alcohol with a methyl α-N-NPEOC-aminoalkylphosphonate using the methods described herein, i.e., using the activating agents triarylphosphine, dialkylazodicarboxylate (such as DIAD or DEAD), and a base. In a preferred embodiment, a triarylphosphine wherein at least of the aryl groups bears an electronegative substituent, and more preferably tris(4-chlorophenyl)phosphine, is used. More preferably, the electronegative substituent(s) will have a Hammett constant(s) from between about 0.05 to about 0.8, and preferably between about 0.25 to about 0.5. These reagents activate the hydroxyl by forming a triphenylphosphonium derivative, which in turn undergoes an $S_N 2$ displacement by the phosphonic acid monoester to afford the phosphonate diester (compound 22, FIG. 6).

Due to the lability of the FMOC group in the presence of the coupling reagents, according to this embodiment, preferred protecting groups include the NPEOC group and NPEOM group. These groups can be removed with 5-10% DBU (1,8-diazabicyclo[5.4.0]undec-7-ene) in NMP (N-methyl pyrrolidone). UV analysis of the 4-nitrostyrene chromophore (308 nm, $\epsilon = 13,200$ M$^{-1}$ cm$^{-1}$) can be performed to determine the coupling efficiency. The CBz-protecting group also can be employed.

Initial experiments were performed on Alltech Adsorbosphere Amino beads (5 μm glass beads derivatized with an amino functionality and a 50-80 μm pore size. Very slow and incomplete coupling was observed, possibly attributable to the small pore size and variations in pore geometries which may have hindered the accessibility of the a-hydroxy acid residues to the bulky protonated betaine. High coupling yields, however, could be obtained using either controlled pore glass (CPG) or a polyethyleneglycol crosslinked polystyrene resin (Rapp Polymere) as the solid substrate. Examples of these yields are shown below in Table 4.

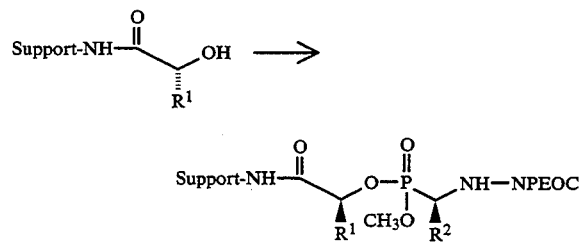

TABLE 4

| R² | Time Required for >90% Coupling[4] | | | |
|---|---|---|---|---|
| | R¹ = H | CH₃ | CH₂(C₆H₅) | CH₂CH(CH₃)₂ |
| H | <0.5 | <1.5 | 12 | 6.4 |
| (R)—CH₃ | <0.5 | <1.5 | 12 | 8.4 |
| (R,S)—CH₂(C₆H₅) | <0.5 | <1.5 | 13 | 10 |
| (R,S)—CH₂CH(CH₃)₂ | <0.5 | <1.5 | 14 | 10 |
| (R,S)—CH(CH₃)₂ | <0.5 | <1.5 | 10 | 20 |

[4] As determined by 4-nitrostyrene absorbance at 308 nm.

Figure 6:
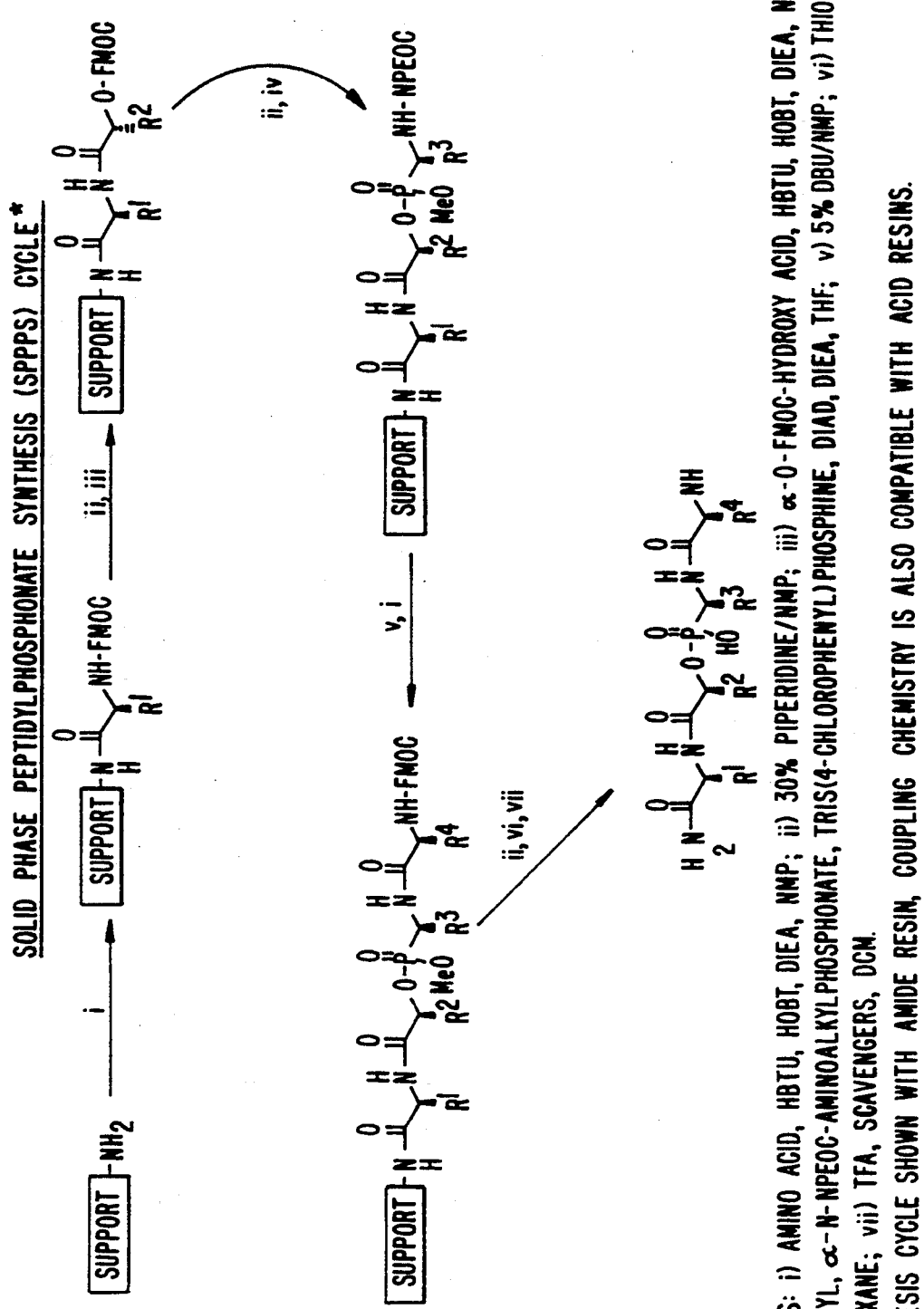
FIG. 6 shows a reaction for incorporating a phosphonate transition state analog pharmacaphore into a growing peptide chain via solid phase synthesis.

Upon completion of the coupling reaction, one has a variety of options: the N-terminal phosphonate can be deprotected to allow further couplings, for example, using standard peptide coupling chemistry, or synthesis can stop here, and the compound can be cleaved from the support, as shown in FIG. 6. One can also selectively hydrolyze the ester by, e.g., treatment with TMSBr or triethylammonium phenoxide, either on the support or after the compound is cleaved from the support.

One skilled in the art will appreciate that the cleavage conditions will vary with the type of substrate and the nature of the phosphonate ester. Typically, the substrate-bound phosphonate ester will first be washed with a polar aprotic solvent and dried under reduced pressure. If a PAC or PAL resin is used as the substrate, then cleavage of the phosphonate ester from the resin can be accomplished through the action of trifluoroacetic acid. The phosphonate ester can be isolated by filtration and concentrated under reduced pressure. The solid phase synthesis of phosphonate esters by the method of the present invention will generally produce phosphonate esters of greater than 75% purity.

The methods described herein are superior to others in which a peptidylphosphonate is synthesized as a dimer and then incorporated as a cassette into a growing peptide. In the prior art methods, one must first synthesize the cassette in solution phase and purify the cassette to homogeneity prior to incorporation. The prior art method allows one to synthesize only one combination of phosphonate-hydroxy acid dimer. One would have to synthesize in solution phase an entirely new cassette to make a different phosphonate.

5. The Building Blocks a. The Hydroxy Acid

Figure 7:
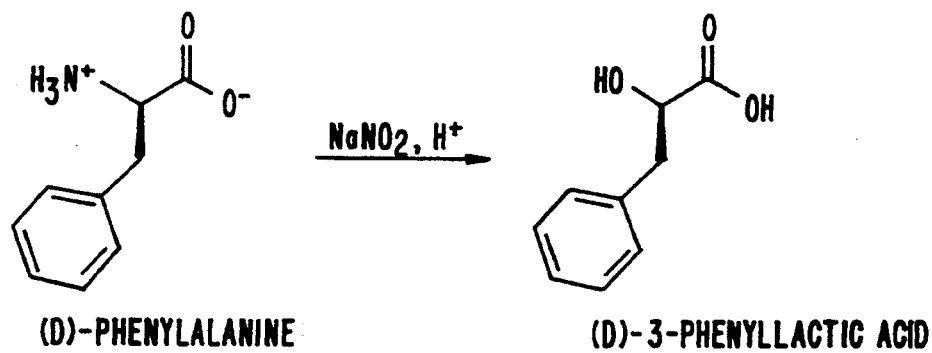
FIG. 7 shows a reaction for converting D-phenylalanine to the corresponding hydroxy acid; this reaction scheme can be used to convert a wide variety of the amino acids to the hydroxy acid counterparts.

By the present method, a single phosphonic acid building block can be coupled to virtually any hydroxy acid to form a variety of different dimers. A number of the hydroxy acids are commercially available. In addition, alpha-hydroxy acid analogs of the amino acids can be prepared in from commercially available amino acids (or any hydroxy acid) using the protocol shown in FIG. 7. For carboxylic acids having additional side chain functional groups, such as serine, threonine, and tyrosine, typically the side chain functional group will be protected (with a protecting group PG) prior to diazotization. Examples of suitable side chain protecting groups include, but are not limited to, t-butyl esters (for Glu and Asp); t-butyl ethers (for Ser, Thr, and Tyr); BOC (for Lys); and trityl amides (for Gln and Asn).

This synthetic route involves (1) diazotization with sodium nitrite in mild acid, such as acetic acid or citric acid; and (2) carboxy protection, preferably as the triisopropylsilyl group, and protection of the hydroxy group, typically with FMOC-Cl; and carboxy deprotection. This reaction sequence is stereospecific and results in retention of the chirality of the carbon bearing the amino group (and thus, the carbon bearing the hydroxyl group). This latter multi-step sequence can be performed without intermediate product isolation and purification. This reaction sequence will generally produce the desired hydroxy acid in 35–70% isolated overall yield.]

b. The Phosphonate

Figure 9:
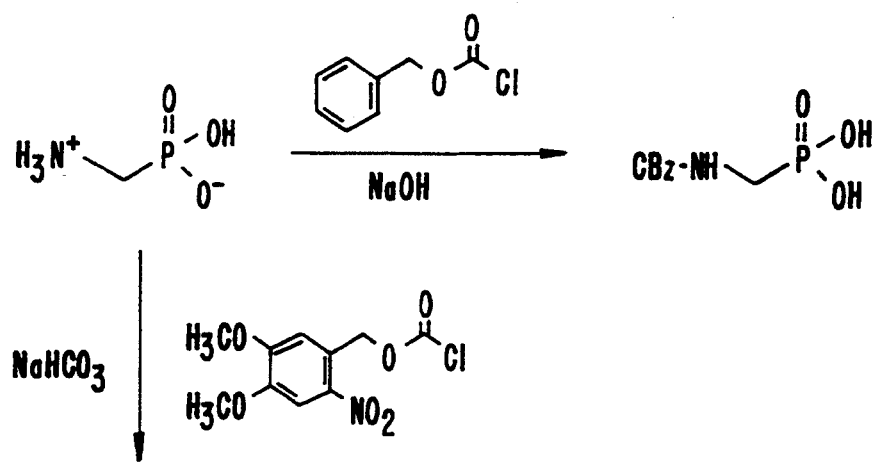
FIG. 9 shows the synthesis of a protected aminophosphonic acid from an aminophosphonic acid and a photoremovable protecting group; this reaction can be used to convert any of the aminophosphonic acids to the protected aminophosphonic acid counterpart.
Figure 8:
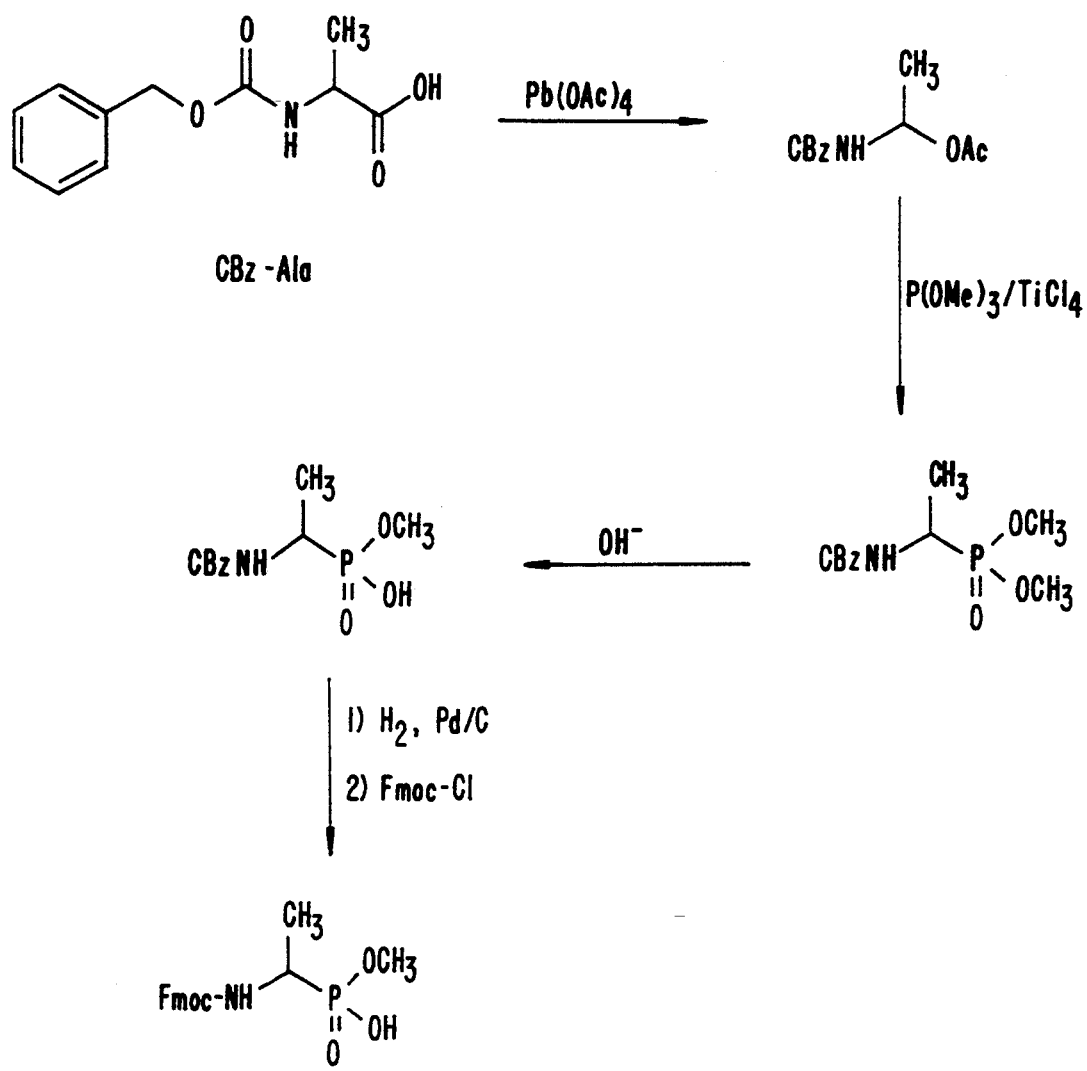
FIG. 8 shows the synthesis of a protected aminophosphonic acid from alanine; this reaction can be used to convert a wide variety of the amino acids to the protected aminophosphonic acid counterparts.

Like the hydroxy acids, phosphonic acid building blocks can be prepared from commercially available amino acids. Again, one should not limit the present invention to only the α-aminoalkylphosphonic acids or phosphonic acids that are similar to the naturally occurring amino acids or the 20 amino acids encoded genetically. The synthesis of a protected aminophosphonic acid starting with a commercially available amino acid is outlined in FIG. 8, and the synthesis of a protected aminophosphonic acid starting with a commercially available aminophosphonic acid is outlined in FIG. 9. As discussed above, α-aminoalkylphosphonic acids can also be produced by the procedures set forth in copending application U.S. Ser. No. (Attorney Docket No. 11509-84), which is incorporated herein by reference.

6. Libraries

The present methods for the solid phase synthesis of phosphonate esters are especially preferred for the production of libraries of peptidylphosphonic acid derivatives. These libraries can be assembled using, for example, the combinatorial synthesis strategies described in PCT patent publication No. 92/10092; U.S. patent application Ser. No. 762,522, filed Sep. 18, 1991; and U.S. patent application Ser. No. 876,792, filed Apr. 29, 1992.

Briefly, a combinatorial synthesis strategy is an ordered strategy for parallel synthesis of diverse polymer sequences by sequential addition of reagents to a solid support. In one embodiment, the solid support is a collection of beads, and each cycle of monomer addition is carried out in parallel in a series of reactions, each reaction using a different monomer. After each cycle, the beads from the different, parallel series of reactions are pooled and redistributed prior to the next cycle of monomer addition. These methods apply, for example, to the synthesis of protease inhibitors where one knows the position of the $P_1$-$P_1'$ site and wants to fix the phosphonate linkage while exploring amino acid preferences at the flanking regions.

In another preferred embodiment, the combinatorial synthesis is performed using the VLSIPS ™ technique described in Fodor et al. (1991) *Science* 251:767–773, and in PCT patent publication No. 92/10092 (and corresponding U.S. counterparts, including Ser. No. 805,727, filed Dec. 6, 1991). Briefly, the VLSIPS ™ technology is a method for synthesizing large numbers of different compounds simultaneously at specific locations on a silica chip. Supra. Using this technology, one can produce an array of phosphonic acid and phosphonate derivatives and screen that array for compounds with biological activity.

To screen for biological activity, the array is exposed to one or more receptors such as antibodies, whole cells, receptors on vesicles, lipids, or any one of a variety of other receptors. The receptors are preferably labeled with, for example, a fluorescent marker, radioactive marker, or a labeled antibody reactive with the receptor. After the array has been exposed to the receptor, the location of the marker can be detected with, for example, photon detection or autoradiographic techniques. Through knowledge of the sequence of the material at the location where binding is detected, one can quickly determine which compounds bind to the receptor.

Figure 10A:
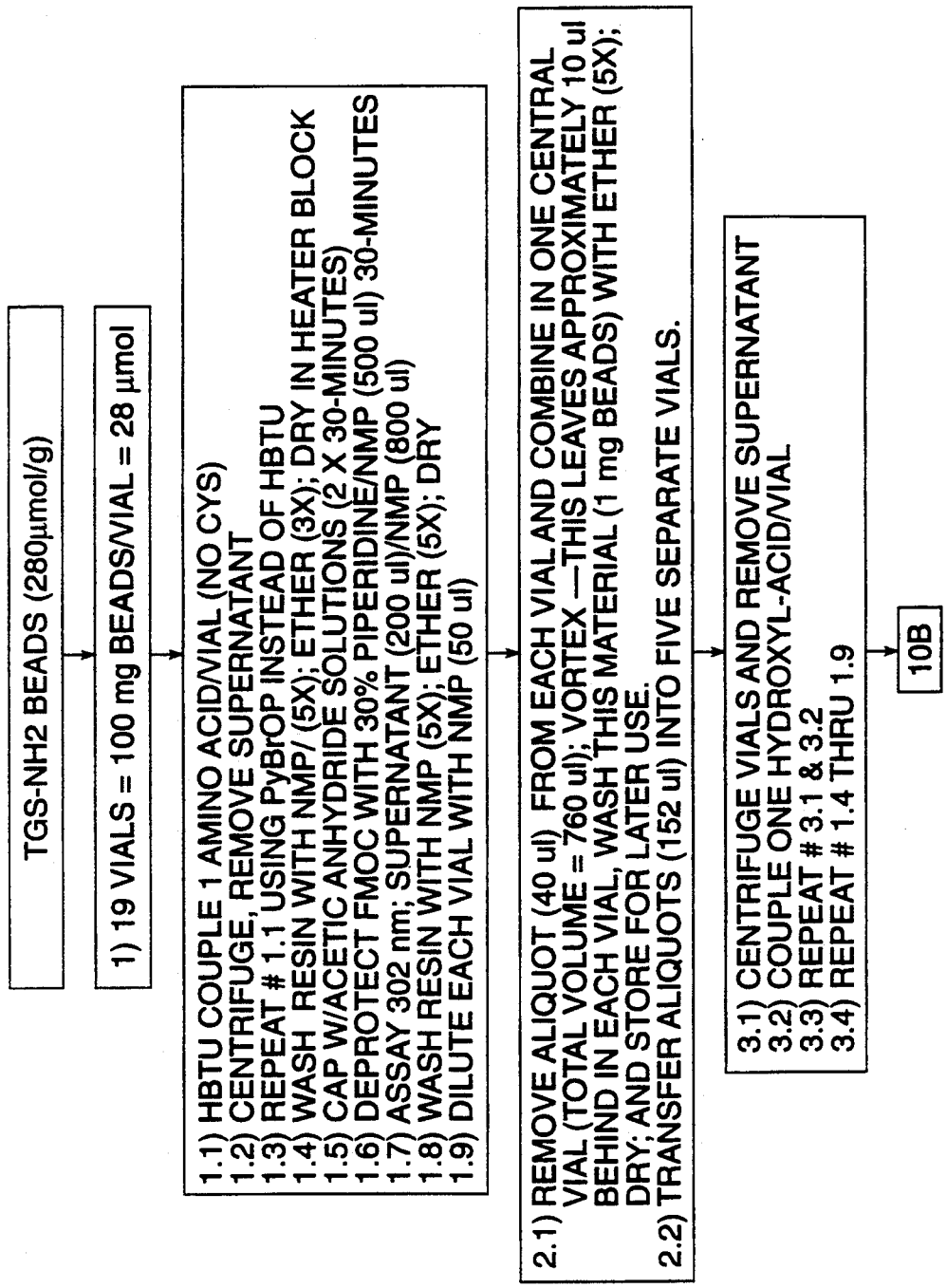
FIG. 10A and B illustrate the synthetic protocol for the solid state synthesis of peptidylphosphonate libraries.

This combinatorial synthesis approach can be utilized to produce a library of peptidylphosphonates using the reaction scheme illustrated in FIG. 6 and the synthetic protocol shown in FIG. 10. Typically, the protecting groups will be present on the amine and hydroxyl functional groups on the surface of the support where coupling occurs and will be photolabile, although other protecting groups can be used to advantage in the protocol. Using lithographic methods, one exposes the photoremovable protecting group to light so as to remove the group from the reactant in the first selected region to free an amine or hydroxyl group on the compounds where the desired attachment is to occur.

The substrate is then washed or otherwise contacted with a first hydroxy acid, amino acid, or phosphonate, depending on the step in the process. Once the hydroxy acid is coupled to the activated amine groups on the support and then irradiated to remove the protecting group from the hydroxyl group of the coupled hydroxy acid, an $\alpha$-aminoalkylphosphonate, preferably a monomethyl $\alpha$-aminoalkylphosphonate, is coupled to the hydroxyl group with the activating reagents dialkylazodicarboxylate and triphenylphosphine. Portions of the substrate which have not been deprotected do not react with the phosphonate (or other monomer, depending on the step and the compounds being synthesized). If the phosphonate (or other monomer) possesses other functionalities, these functionalities may need to be blocked with an appropriate protecting group, which may be photolabile but could also be removable with acid or base treatment.

A second set of selected regions can then be exposed to light to remove the photoremovable protecting group from compounds in the second set of regions. The substrate is then contacted with a second monomer and coupling reagents, e.g., a monomethyl phosphonate, triphenylphosphine, and dialkylazodicarboxylate. Of course, one can also introduce and couple other monomers, such as amino acids, to the growing polymer chains on the surface, so long as appropriate chemistry and protecting groups are employed. This process is repeated until the desired array of compounds has been synthesized.

Thus, libraries of potential ligands for binding with receptors can be prepared using the methods of the present invention. Typically, a peptide would first be identified as a potential ligand for binding with a given receptor. An array of peptide analogues would then be produced. These analogues are peptidylphosphonates in which amide linkages of the peptide have been replaced with a phosphonate linkage. Of course, one can also synthesize other polymers, such as polyphosphonates (using $\alpha$-hydroxy alkylphosphonates), by the methods of the invention.

The methods described herein have been employed to produce libraries of a combinatorial libray of $\alpha$-N-CBz-aminoalkylphosphonic acid capped trimers on both cleavable and nonocleavable resin. Thermolysin, a well characterized metalloprotease, has been used as a model system to investigate a number of assay formats, both with soluble and resin supported libraries.

III. Synthesis of Phosphonate Diesters

A. Overview

Figures 11, 12:
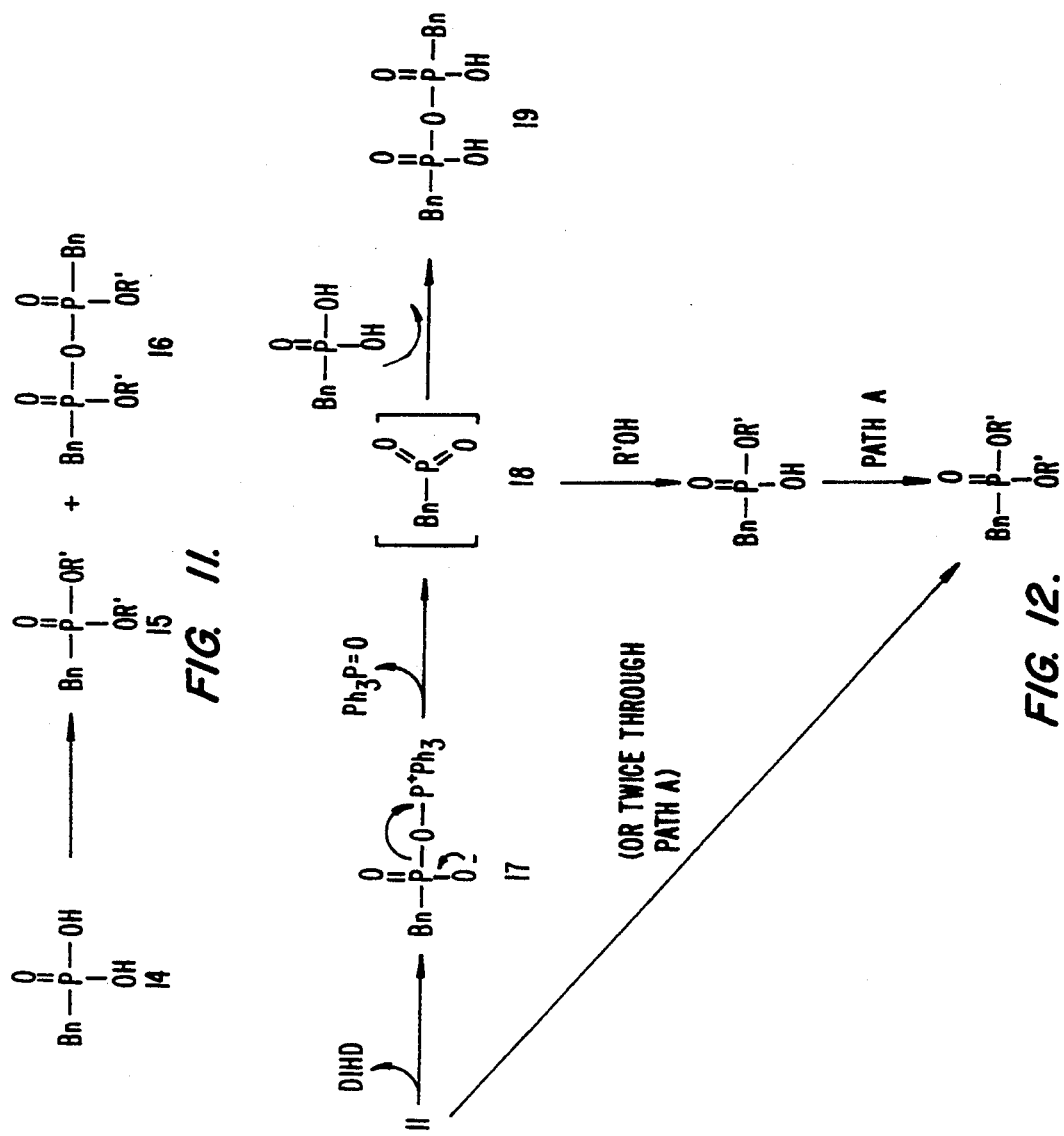
FIG. 11 shows the reaction for producing one type of symmetrical phosphonate diester (compound 15).
FIG. 12 shows a theoretical reaction mechanism for the observed reactivity of benzylphosphonic acid.

Thus, the present invention has diverse applications. For instance, and as shown in FIG. 11, the present invention also provides methods to synthesize symmetrical phosphonate diesters (compound 15). Bisesterification of commercially available benzylphosphonic acid (compound 14, FIG. 11, commercially available from Lancaster Synthesis) was initially used to exemplify this aspect of the invention, and the reaction was carried out by adding a dialkylazodicarboxylate, preferably DIAD, to a solution of compound 14, an alcohol, and a triarylphosphine, preferably triphenylphosphine, in THF. When primary alcohols were used, the reaction was instantaneous, and the symmetrical esters were isolated in high yields.

According to a preferred embodiment, approximately equimolar amounts of the triarylphosphine, the dialkylazodicarboxylate, and the alcohol are used. Typically, the ratio of phosphonic acid to alcohol will range from about 1:2.5 to about 1:50, and preferably from about 1:2.5 to about 1:25.

B. The General Reaction

The general procedure for the solution phase synthesis of benzylphosphonate diesters is as follows. To a solution of benzylphosphonic acid (0.5 mmol), alcohol (1.25 mmol), and triphenylphosphine (1.25 mmol) dissolved in anhydrous THF (5 mL), is added diisopropylazodicarboxylate (1.25 mmol). After about 30 minutes, the reaction mixture is concentrated under vacuum, and then the triphenylphosphineoxide is crystallized with acetone/pentane, and removed by filtration. The filtrate is optionally concentrated under vacuum and purified by chromatography (HOAc/EtOAc can be used). Illustrative compounds prepared by this protocol include dimethyl benzylphosphonate, diisopropyl benzylphosphonate, and dibenzyl benzylphosphonate. See Example 2.

C. The Mechanism

To understand the method for making phosphonate diesters, one may benefit from considering the reaction schemes shown in FIGS. 3 (supra) and 12. When methanol and benzyl alcohol were used, the alkoxyphosphorane formed reacted cleanly and rapidly with benzylphosphonic acid to form the phosphonate diesters. With isopropanol, the reaction was complicated by the ready decomposition of compound 12 (FIG. 3), presumably via an E2 elimination as has been observed by others (see Von Itzstein and Jenkins, supra, and Loibner and Zbiral (1977) *Helv. Chim. Acta.* 60:417).

One explanation for the observed reactivity of benzylphosphonic acid is that intramolecular dehydration of compound 11 (FIGS. 3 and 12) yields benzylmetaphosphonate (compound 18, FIG. 12), triphenylphosphine oxide, and diisopropylhydrazodiformate (see FIG. 12). Formation of phenylmetaphosphonate (see Eckes and Regitz (1975) *Tetr. Lett.*, p.447 et seq.), mesitylenemetaphosphonate (see Sigal and Lowe (1978) *J. Am. Chem. Soc.* 100:6394), and monomeric metaphosphate (see Bodalski et al. (1991) *J. Org. Chem.* 56:2666;

Freeman et al. (1987) *J. Am. Chem. Soc.* 109:3166; and Westheimer (1981) *Chem. Rev.* 81:313) have all been observed. The benzylmetaphosphonate (compound 18, FIG. 12) would be highly electrophilic and could readily undergo nucleophilic attack by t-butanol to produce the t-butyl ester, or by another molecule of benzylphosphonic acid producing benzylpyrophosphonate (compound 19, FIG. 12). Mitsunobu esterification of compound 19 (FIG. 12) with isopropanol would then yield diisopropyl benzylpyrophosphonate (compound 16, FIG. 11).

D. The Results

The results of these experiments are shown in Table 5 below.

TABLE 5

Symmetrical alkylphosphonate diester syntheses via condensations of benzylphosphonic acid and alcohols

| Reaction Scheme* | Alcohol | Alcohol Equivalents | Yield |
|---|---|---|---|
| A | Methanol | 2.5 | 85% |
| A | Methanol | 25 | 91% |
| A | Isopropanol | 2.5 | 11% |
| A | Isopropanol | 25 | 76% |
| A | Benzyl alcohol | 2.5 | 87% |
| B | Methanol | 5 | 81% |
| B | Isopropanol | 5 | 37% |
| B | Benzyl alcohol | 5 | 90% |

*See discussion below.

When isopropanol was used, diisopropyl benzylpyrophosphonate (compound 16, FIG. 11, where R' is isopropanol) was the major product. Similar products have been observed during the study of radical-based dephosphorylation in the production of monomeric metaphosphate. See Avila and Frost (1988) *J. Am. Chem. Soc.* 110:7904. Perturbations of the reaction conditions yielded mixed results: temperatures of −78° C. to 25° C. had no effect on the product ratios, and changing the concentration of the reactants likewise had no effect on the product ratios. However, as shown in Table 2, increasing the equivalents of the alcohol to the phosphonic acid improves the yield markedly. In similar fashion, reaction scheme B, described more fully below, could also be accessed to improve yields; however, this method may be problematic if the reaction intermediates are susceptible to elimination or degradation reactions (as is isopropanol; see Table 2).

Thus, the present invention provides a variety of methods for making, using, and screening phosphonate esters and compounds comprising phosphonate esters. The above description and the following examples are intended to be illustrative and not restrictive. Many embodiments of the invention not explicitly set forth herein will be apparent to those of skill in the art upon reviewing this description of the invention. The disclosures of all articles and references, including patents and patent applications, in their entirety are incorporated herein by reference. The scope of the invention should be determined not with reference to the above description, but instead with reference to the appended claims, along with the full scope of equivalents to which such claims are entitled.

The following examples are provided to aid one of skill in the art in understanding the invention. Isolation and purification of the compounds and intermediates described in the examples can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures are in the examples below. Other equivalent separation or isolation procedures can, of course, also be used. These examples are for illustrative purposes only and are not to be construed as limiting this invention in any manner.

EXPERIMENTAL $^1$H-NMR spectra were recorded at 300 MHz. Mass spectral measurements were performed by the Mass Spectrometry Laboratory at the University of California, Berkeley.

Benzylphosphonic acid, tris(pentafluorophenyl), tris(4-fluorophenyl)-phosphine, and tris(4-chlorophenyl)phosphine were purchased from Lancaster Synthesis Inc., glycolic acid, D-lactic acid, 3-D-phenyllactic acid, and a-D-hydroxyisovaleric acid from Fluka, and all remaining chemicals were purchased from Aldrich Chemical Co. THF was refluxed over potassium and distilled prior to use.

EXAMPLE 1

Preparation of Phosphonic Acid Monoesters 1.1 The Phosphonate as the Limiting Reagent To a solution of methyl alkylphosphonate (0.5 mmol), an alcohol (0.75 mmol), and triphenylphosphine (0.75 mmol) in anhydrous THF, was added diisopropylazodicarboxylate (0.75 mmol). Upon completion of the condensation reaction, TMSBr was added. Stirring was continued an additional hour. The reaction mixture was diluted with ether (10 mL), and extracted with 5% aqueous sodium bicarbonate (10 mL×2). The aqueous phase was washed with ether (10 mL×2), acidified to pH=2 with concentrated hydrochloric acid, and extracted with ethyl acetate (10 mL×3). The ethyl acetate phase was dried over magnesium sulfate, filtered, and concentrated under reduced pressure to yield a phosphonic acid monoester.

1.2 The Alcohol as the Limiting Reagent

To the methyl alkylphosphonate (1.5 mmol), dissolved in THF (10 ml) was added tris(4-chlorophenyl)-phosphine (1.5 mmol), DIAD (1.5 mmol) and DIEA (5 mmol) followed by the alcohol (1 mmol). Upon completion of the reaction the mixture was concentrated under vacuum then purified by flash chromatography (EtOAc/hexanes).

Following this procedure the following compounds were prepared:

methyl isopropyl benzylphosphonate: $^{13}$C-NMR (CDCl$_3$) ∂: 131.40 (d, J=9 Hz), 129.72 (d, J=7 Hz), 128.42 (d, J=3 Hz), 126.76 (d, J=4 Hz), 70.89 (d, J=7 Hz), 52.31 (d, J=7 Hz), 33.75 (d, J=139 Hz), 24.00 (d, J=4 Hz), 23.66 (d, J=6 Hz). $^{31}$P-NMR ∂: 27.15. MS (FAB+, m/z): 228. Anal. Calcd. for C$_{11}$H$_{17}$O$_3$P.0.6H$_2$O: C, 55.26; H, 7.69; P, 12.95. Found: C, 55.05; H, 7.29;

methyl L-2-[(methyl benzylphosphoryl)oxy]acetate: $^{13}$C-NMR (CDCl$_3$) ∂: 168.86 (d, J=4 Hz), 130.84 (d, J=10 Hz), 129.75 (d, J=7 Hz), 128.53 (d, J=3 Hz), 126.98 (d, J=4 Hz), 62.39 (d, J=4 Hz), 52.54 (d, J=7 Hz), 52.16, 33.51 (d, J=139 Hz). $^{31}$P-NMR ∂: 29.67. MS (FAB+, m/z): 258;

methyl L-2-[(methyl benzylphosphoryl)oxy]propionate: $^{13}$C-NMR (CDCl$_3$) ∂: 171.52, 131.14 (d, J=10 Hz), 130.87 (d, J=9 Hz), 129.78 (d, J=7 Hz), 128.49, 128.40 (d, J=3 Hz), 127.00 (d, J=4 Hz), 126.82 (d, J=4 Hz), 70.64 (t, J=7 Hz), 52.69 (d, J=7 Hz), 52.31, 52.25, 52.06

(d, J=7 Hz), 33.69 (d, J=140 Hz), 33.62 (d, J=139 Hz), 19.34 (d, J=4 Hz), 18.81 (d, J=6 Hz). $^{31}$P-NMR ∂: 28.99, 28.44. MS (FAB+,m/z): 272. Anal. Calcd. for $C_{12}H_{17}O_5P \cdot 0.5H_2O$: C, 51.24; H, 6.46; P, 11.01. Found: C, 51.17; H, 6.46;

methyl L-2-[(methyl benzylphosphoryl)oxy]-3-phenylpropionate: $^{13}$C-NMR (CDCl$_3$) ∂: 170.59, 135.72 (d, J=7 Hz), 129.86 (d, J=7 Hz), 129.69 (d, J=7 Hz), 129.50, 128.50, 128.43, 128.34, 127.13, 127.01, 126.86 (d, J=3 Hz), 126.74 (d, J=4 Hz), 75.80 (d, J=7 Hz), 74.94 (d, J=7 Hz), 52.73 (d, J=8 Hz), 52.39, 52.26, 51.53 (d, J=7 Hz), 39.23, 39.15, 39.09, 33.71 (d, J=140 Hz), 33.33 (d, J=140 Hz). $^{31}$p-NMR ∂: 28.89. MS (FAB+, m/z): 348. Anal. Calcd. for $C_{11}H_{17}O_3P \cdot 0.5H_2O$: C, 60.49; H, 6.22; P, 8.67. Found: C, 60.49; H, 6.22;

methyl L-2-[(methyl benzylphosphoryl)oxy]-3-methylbutyrate: $^{13}$C-NMR (CDCl$_3$) ∂: 170.72 (d, J=6 Hz), 131.54 (d, J=10 Hz), 131.04 (d, J=9 Hz), 129.92 (d, J=6 Hz), 129.80, 128.53 (d, J=3 Hz), 128.36 (d, J=3 Hz), 126.98 (d, J=4 Hz), 126.75 (d, J=4 Hz), 79.01 (d, J=7 Hz), 78.63 (d, J=7 Hz), 53.09 (d, J=7 Hz), 52.29 (d, J=7 Hz), 52.44, 52.02, 33.77 (d, J=139 Hz), 33.50 (d, J=141 Hz), 31.57, 31.49, 18.64, 18.27, 16.76, 16.49. $^{31}$P-NMR ∂: 29.17, 28.47. MS (FAB+, m/z): 300;

methyl L-2-[[methyl[1-[N-(benzyloxycarbonyl)amino]-methyl]-phosphoryl]oxy]propionate: $^{13}$C-NMR (CDCl$_3$) ∂: 171.76, 171.23, 156.18, 156.10, 136.26, 136.14, 128.44, 128.41, 128.15, 128.03, 71.00, 70.91, 70.82, 67.18, 67.10, 53.71 (d, J=7 Hz), 52.71, 52.46, 52.27 (d, J=6 Hz), 36.86 (d, J=160 Hz), 36.75 (d, J=157 Hz), 19.12, 19.05. $^{31}$P-NMR ∂: 25.51, 24.01. MS (FAB+, m/z): 346. Anal. Calcd. for $C_{11}H_{17}O_3P$: C, 48.70; H, 5.84; N, 4.06; P, 8.97. Found: C, 48.88; H, 6.08; N, 3.94; P, 8.87;

methyl L-2-[[methyl[1-[N-(benzyloxycarbonyl)amino]methyl]-phosphoryl]oxy]-3-phenylpropionate: $^{13}$C-NMR (CDCl$_3$) ∂: 170.99, 170.25, 156.14 (d, J=7 Hz), 155.87 (d, J=8 Hz), 136.25 (d, J=13 Hz), 135.67 (d, J=6 Hz), 129.41, 129.29, 128.80, 128.61, 128.17, 128.19, 128.08, 127.48, 127.21, 75.33 (d, J=7 Hz), 75.14 (d, J=6 Hz), 67.18, 67.13, 53.04 (d, J=7 Hz), 52.83, 52.58, 51.69 (d, J=7 Hz), 39.03 (d, J=6 Hz), 38.92 (d, J=6 Hz) 37.10 (d, J=160 Hz), 36.54 (d, J=160 Hz). $^{31}$P-NMR ∂: 25.24, 24.45. MS (FAB+, m/z): 422. Anal. Calcd. for $C_{11}H_{17}O_3P$: C, 57.00; H, 5.75; N, 3.32; P, 7.35. Found: C, 56.65; H, 6.07; N, 3.41;

methyl L-2-[[methyl[1-[N-(benzyloxycarbonyl)amino]methyl]phosphoryl]oxy]-3-methylbutyrate: $^{13}$C-NMR (CDCl$_3$) ∂: 171.25, 170.49, 156.25, 156.17, 156.05, 136.35, 136.16, 133.35, 133.20, 128.48, 128.45, 128.18, 128.07, 79.20 (d, J=8 Hz), 79.05 (d, J=6 Hz), 67.23, 67.11, 53.38 (d, J=7 Hz), 52.56, 52.47, 52.27, 36.93 (d, J=158 Hz), 36.64 (d, J=160 Hz), 31.40, 31.30, 18.81, 18.51, 16.47, 16.21. $^{31}$P-NMR ∂: 25.88, 24.31. MS (FAB+, m/z): 374;

methyl L-2-[[methyl[(R)-1-[N-(benzyloxycarbonyl)amino]ethyl]-phosphoryl]oxy]propionate: $^{13}$C-NMR (CDCl$_3$) ∂: 171.35, 171.31, 155.65, 155.55, 155.52, 136.34, 136.17, 128.43, 128.37, 128.13, 128.01, 127.95, 70.97 (d, J=8 Hz), 70.57 (d, J=7 Hz), 67.04, 66.93, 53.20 (d, J=7 Hz), 52.64, 52.42, 52.29, 43.66 (d, J=160 Hz), 43.38 (d, J=169 Hz), 19.13 (d, J=4 Hz), 18.94 (d, J=6 Hz), 16.27, 15.88. $^{31}$P-NMR ∂: 27.76, 26.96. MS (FAB+, m/z): 360. Anal. Calcd. for $C_{11}H_{17}O_3P$: C, 50.13; H, 6.18; N, 3.90; P, 8.62. Found: C, 49.79; H, 6.23; N, 4.14;

methyl L-2-[[methyl[(R)-1-[N-(benzyloxycarbonyl)amino]ethyl]-phosphoryl]oxy]-3-phenylpropionate: $^{13}$C-NMR (CDCl$^{13}$) ∂: 170.92, 170.89, 170.32, 155.47, 155.36, 136.42, 136.20, 135.68, 135.39, 129.45, 129.37, 128.64, 128.51, 128.43, 128.37, 128.10, 127.96, 127.93, 127.30, 127.12, 75.34 (d, J=7 Hz), 74.87 (d, J=7 Hz), 66.99, 66.86, 53.25 (d, J=7 Hz), 52.71 52.40, 51.69 (d, J=7 Hz), 43.81 (d, J=160 Hz), 43.37 (d, J=160 Hz), 39.12, 39.03, 38.96, 16.36, 15.58. $^{31}$P-NMR ∂: 27.51, 26.77. MS (FAB+, m/z): 436. Anal. Calcd. for $C_{11}H_{17}O_3P \cdot 0.2H_2O$: C, 57.44; H, 6.07; N, 3.19; P, 7.05. Found: C, 57.44; H, 6.30; N, 3.19;

methyl L-2-[[methyl[(R)-1-[N-(benzyloxycarbonyl)-amino]ethyl]-phosphoryl]oxy]-3-methylbutyrate: $^{13}$C-NMR (CDCl$_3$) ∂: 171.14, 171.10, 170.67, 155.73, 136.48, 136.25, 128.17, 128.41, 128.14, 127.98, 79.18 (d, J=9 Hz), 78.75 (d, J=7 Hz), 67.04, 66.92, 53.56 (d, J=7 Hz), 52.71 (d, J=7 Hz), 52.50, 52.24, 43.98 (d, J=159 Hz), 43.38 (d, J=160 Hz), 31.53, 31.45, 31.39, 18.78, 18.48, 16.56, 16.51, 16.31, 16.21.31. $^{31}$P-NMR ∂: 28.07, 27.10. MS (FAB+,m/z): 388. Anal. Calcd. for $C_{11}H_{17}O_3P$: C, 52.71; H, 6.77; N, 3.62; P, 8.00. Found: C, 52.33; H, 6.84; N, 3.71;

methyl L-2-[[methyl[(R,S)-1-[N-(benzyloxycarbonyl)-amino]-2-methylpropyl]phosphoryl]oxy]propionate: $^{13}$C-NMR (CDCl$_3$) ∂: 171.39, 171.36, 171.31, 156.34, 156.25, 156.17, 136.33, 136.28, 136.22, 136.15, 128.37, 128.05, 127.91, 127.84, 70.80, 70.69, 70.57, 70.49, 70.41, 70.35, 67.07, 67.01, 66.95, 54.06, 54.00, 53.81, 53.07, 52.98, 52.77, 52.67, 52.44, 52.41, 52.29, 52.13, 52.03, 51.97, 51.76, 29.17, 29.11, 29.06, 28.95, 28.89, 28.78, 28.72, 20.35, 20.30, 20.22, 20.13, 19.48, 19.44, 19.24, 19.19, 19.02, 18.93, 18.84, 17.81, 17.71, 17.65, 17.56. $^{31}$P-NMR ∂: 27.08, 26.13, 26.03;

methyl L-2-[[methyl[(R,S)-1-[N-(benzyloxycarbonyl)-amino]-2-methylpropyl]phosphoryl]oxy]-3-phenylpropionate: $^{13}$C-NMR (CDCl$_3$) ∂: 170.35, 156.22 (m), 136.29 (m), 135.38 (m), 129.47, 129.41, 128.51, 128.44, 128.17, 128.10, 128.05, 127.99, 127.90, 127.18, 127.10, 74.94 (m), 67.09 (m), 54.04 (m), 53.19 (m), 52.30 (m), 39.19 (m), 29.18 (m), 20.35 (m), 17.78 (m). $^{31}$P-NMR ∂: 27.09, 26.85, 26.15, 26.00;

methyl L-2-[[methyl[(R,S)-1-[N-(benzyloxycarbonyl)-amino]-2-methylpropyl]phosphoryl]oxy]-3-methylbutyrate: $^{13}$C-NMR (CDCl$_3$) ∂: 170.78, 156.52, 156.42, 136.50, 128.46, 128.40, 128.16, 128.01, 127.96, 127.89, 78.77 (m), 67.03 (m), 54.40 (m), 52.35 (m), 31.48 (m), 29.28 (m), 20.52 (m), 18.70 (m), 17.79 (m), 16.57 (m). $^{31}$P-NMR ∂: 27.64, 27.24, 26.48, 26.08. Anal. Calcd. for $C_{11}H_{17}O_3P$: C, 54.93; H, 7.28; N, 3.37; P, 7.46. Found: C, 55.19; H, 7.24; N, 3.36.

EXAMPLE 2

Preparation of Phosphonate Diesters 2.1 Method A

To a solution of benzylphosphonic acid (0.5 mmol), an alcohol, and triphenylphosphine (1.25 mmol) in anhydrous THF (5 mL), was added diisopropylazodicarboxylate (1.25 mmol). After 30 minutes, the reaction mixture was concentrated under reduced pressure. The triphenylphosphineoxide was crystallized with acetone/pentane and removed by filtration. The filtrate was concentrated under reduced pressure and purified by chromatography (elution with acetic acid/ethyl acetate) to yield a phosphonate diester.

2.2 Method B

To a solution of an alcohol and triphenylphosphine (1.25 mmol) in anhydrous THF (5 mL), was added diisopropylazodicarboxylate (1.25 mmol). To the reaction mixture was then added a solution of benzylphosphonic acid (0.5 mmol) in anhydrous THF. After 30 minutes, the reaction mixture was concentrated under reduced pressure. The triphenylphosphineoxide was crystallized with acetone/pentane and removed by filtration. The filtrate was concentrated under reduced pressure and purified by chromatography (elution with acetic acid/ethyl acetate) to yield a phosphonate diester.

EXAMPLE 3

Synthesis of Phosphonic Acid Building Blocks from Amino Acids 3.1 Preparation of Fmoc-protected Methyl Hydrogen [(±)-N-(fluorenylmethoxycarbonyl)-1-aminoethyl]-phosphonate To an ice-cold solution of lead tetraacetate (34.1 g, 105 mmol) in 100 mL of dimethylformamide (DMF), was added dropwise a solution of CBz-alanine (20.0 g, 89.6 mmol) in 50 mL of DMF. The dark brown reaction mixture was allowed to warm to room temperature and then stirred for 8 hours. The now clear reaction mixture was diluted with saturated sodium bicarbonate (150 mL), extracted with ethyl acetate (4×100 mL), and the combined organic layers washed with saturated sodium bicarbonate (1×100 mL) and then brine (1×100 mL). The organic layer was dried over anhydrous magnesium sulfate and then concentrated to afford 18.52 g of a white solid (93%).

To the acetate (18.52 g, 83.3 mmol) in 333 mL of dichloromethane was added trimethylphosphite, the solution was cooled to −78° C., and 1.0M titanium tetrachloride in dichloromethane solution (100 mL, 100 mmol) was added dropwise over 3 minutes. The reaction was allowed to warm to room temperature and then stirred overnight. The reaction was quenched by the addition of solid sodium carbonate (41.7 g, 146 mmol), stirred for 2 hours, and then filtered through a glass wool plug. The filtrate was washed with water (4×100 ml), brine (1×100 mL), dried over magnesium sulfate, filtered, concentrated to a light yellow oil, and then purified by silica gel chromatography (8:2 ethyl acetate/hexane) to afford 14.06 g of a light yellow oil (59%).

To a solution (10.0 g, 35 mmol) of the light yellow oil (dimethyl [1-[N-(benzyloxycarbonyl)amino]-ethyl]-phosphonate) in ethyl alcohol (218 mL), was added 10M aqueous sodium hydroxide (8.75 mL, 87.5 mmol), and the reaction heated to reflux for 90 minutes. The reaction was cooled, diluted with water (50 mL), acidified to pH=2 with concentrated HCl, and then extracted with ethyl acetate (3×50 mL). The combined organic layers were dried over magnesium sulfate, filtered, and then concentrated to afford 6.73 g of an oily semi-solid (70%).

To a solution (1.0 g, 3.60 mmol) of the oily semi-solid (methyl [1-[N-(benzyloxycarbonyl)amino]-ethyl]phosphonate) in methanol (18 mL) cooled to 0° C., was added 10% Pd/carbon (100 mg) and a balloon of hydrogen gas. The reaction was warmed to room temperature and stirred overnight. The solution was then filtered through a sintered glass funnel and then concentrated to a solid. To some of this solid (100 mg, 0.92 mmol), was added dioxane (1.9 mL), 10% aqueous sodium bicarbonate (1.9 mL), and a solution of 9-fluorenylmethyloxycarbonyl (Fmoc) chloroformate (310 mg, 1.2 mmol) in 1 mL of dioxane, and the slightly turbid reaction mixture was stirred overnight. The now clear reaction mixture was diluted with water and then acidified to pH1 with concentrated HCl. Upon standing, a white precipitate formed. This precipitate was collected by filtration and dried in vacuo to afford 100 mg of an off-white solid (30%).

3.2 Preparation of Methyl Hydrogen [(±)-N-(phenyl-methoxycarbonyl)-1-amino-2-methylpropyl]phosphonate To a suspension of lead tetraacetate (6.537 g, 14.7 mmol) in dry N,N-dimethylformamide (20 mL) under argon at 0° C., was added N-(carbobenzyloxy)-L-valine (3.082 g, 12.3 mmol). After 1 hour, cooling was stopped and stirring continued an additional 3 hours at room temperature. The reaction was quenched with saturated NaHCO$_3$ (100 mL) and extracted with ethyl acetate (4×30 mL). The organic layers were combined, washed with saturated NaHCO$_3$ (25 mL), then with H$_2$O (25 mL), and then brine (25 ml), and then dried over MgSO$_4$, filtered, and concentrated under vacuum.

The resulting oil was dissolved in methylene chloride (20 mL), then trimethylphosphite (2.2 mL, 18.7 mmol) was added, and the mixture was cooled to −78° C. Then, TiCl4 (15 mL, 15 mmol), as a 1M solution in methylene chloride, was added to the mixture. The reaction was warmed to room temperature, and after 12 hours, the reaction mixture was cooled to 0° C., quenched with Na$_2$CO$_3$ (35 g, 120 mmol), and then stirred at room temperature for 30 minutes. The mixture was diluted with H$_2$O (100 mL), extracted with CH$_2$Cl$_2$ (4×25 mL), and the combined organic layers were then washed with H$_2$O (25 ml) and brine (2×25 mL), dried over MgSO$_4$, filtered, then concentrated to afford 3.855 g (99%) of a colorless oil.

EXAMPLE 4

Synthesis of Phosphonic Acid Building Blocks from Aminophosphonic Acids 4.1 Preparation of N-phenylmethoxycarbonyl-amino Methylphosphonic Acid To aminomethylphosphonic acid (500 mg, 4.50 mmol) in 1M aqueous sodium hydroxide (11.5 mL, 11.5 mmol) cooled to 0° C., was added benzyoxycarbonyl chloroformate (845 mg, 5.00 mmol, 0.71 mL) dropwise over one minute and the reaction stirred overnight. The reaction mixture was then extracted with ethyl ether (3×25 mL), the aqueous layer strongly acidified with concentrated HCl, and then extracted with ethyl acetate (3×25 mL). The organic layers were combined, dried (MgSO$_4$), filtered, and then concentrated to afford 700 mg of a white solid (63%).

4.2 Preparation of N-nitroveratryloxycarbonyl-aminomethylphosphonic Acid

To aminomethylphosphonic acid (500 mg, 4.50 mmol) in 5% aqueous sodium bicarbonate (22.5 mL, 13.5 mmol), was added dioxane (20 mL) and then nitroveratryloxycarbonyl (NVOC) chloroformate (5.00 mmol, 1.36 g) in 20 mL of dioxane. The reaction was stirred overnight, extracted with ethyl ether (3×40 mL), and then the aqueous layer was strongly acidified with concentrated HCl. Upon standing, fine yellow needles formed and were filtered and dried in vacuo to afford 1.35 g of product (86%).

EXAMPLE 5

Preparation of a-Hydroxy Acids from α-Amino Acids 5.1 Method A

To D-phenylalanine (2.00 g, 12.4 mmol) in water (20 mL), was added 3M HCl (20 mL, 60 mmol) and acetic acid (10 mL). The solution was cooled to 0° C., and an aqueous solution of sodium nitrite (3.92 g, 56.8 mmol, in 7.5 mL of water) was added dropwise over 10 minutes. The reaction was stirred for eight hours, then more sodium nitrite was added (3.92 g, 56.8 mmol, in 7.5 mL of water). After six hours, the solution was washed with ether (3×25 mL), and the combined organic layers were extracted with saturated sodium bicarbonate (3×30 mL). The bicarbonate washes were combined, acidified to pH 1 with concentrated HCl, and then extracted with ether (3×30 mL). The organic layers were combined, dried (magnesium sulfate), filtered, and then concentrated to afford 1.65 g of a white waxy solid (80%).

5.2 Preparation of (D)-O-nitroveratryloxy-methoxy-2-oxy-4-methylpentanoic Acid

The hydroxy acid prepared above was esterified using diazomethane, and to the resulting compound, methyl (D)-2-hydroxy-4-methyl valerate (1.0 g, 6.85 mmol) in 10 mL of methylene chloride was added Nvom chloride (2.69 g, 10.5 mmol) and diisopropylethyleneamine (DIE& 1.8 mL). After 12 hours, the reaction mixture was diluted with methylene chloride (20 mL), washed with water (2×15 mL), and the organic layer dried (over MgSO4). The product was purified by silica gel chromatography (4:1 petroleum ether:ethyl acetate) to afford 1.2 g of material (47%). The free acid was obtained in quantitative yield by hydrolysis with lithium hydroxide, as previously described. One could also prepare this compound, with possibly higher yield and shorter reaction time, using sodium hydride/THF instead of DIEA/dichloromethane.

5.3 Preparation of Side Chain Functionalized α-O-FMOC-Hydroxy Acids

To a solution of the hydroxy acid prepared above (with the side chain functionality protected, 1 mmol) in dry pyridine at 0° C. is added N-methylmorpholine (2.5 mmol) and triisopropylsilyl chloride (1.1 mmol). The solution was stirred for 15 minutes. To the reaction mixture is then added FMOC-Cl (1.1 mmol) and additional Nomethylmorpholine. The reaction is stirred for 4–8 hours until complete. To the mixture is then added tetrabutylammonium fluoride (2.5 mmol). The reaction mixture is stirred for 15 minutes and quenched.

EXAMPLE 6

Synthesis of a Peptidylphosphonate: Preparation of Z-Phe$^P$(O)-Leu-Ala 6.1 Coupling (D)-Nvom-2-oxy-4-methylpentanoic Acid to Ala Resin To alanine-derivatized PAC resin (1.00 g, 534 gmol) swollen in DMF (5 mL) was added Nvom-2-oxy-4-methylvaleric acid (1.5 mmol, 537 mg), HBTu (1.5 mmol, 720 mg), HOBt (1.5 mmol, 229 mg), and DIEA (3.75 mmol, 650 μL), and the suspension was shaken for one hour. The resin was washed with DMF (4×10 mL), suspended in 30 mL of DMF, and photolyzed at 360 nm (10 mW) for 24 hours. The resin was washed with DMF (4×10 mL) and then with methanol (4×10 mL) and then dried in vacuo.

6.2 Coupling Methyl Hydrogen [(±)-N-(phenylmethoxy-carbonyl)-1-aminoethyl]phosphonate to 2-hydroxy-4-methylvaleryl Alanine Resin Preparation of (±)CBz-Phe$^P$-(O)-Leu-Ala To 2-hydroxy-4-methylvalerylalanine resin (50 mg, 26.5 μgmol) in THF was added methyl hydrogen [(±)-N-(phenylmethoxycarbonyl)-1-aminoethyl]phosphonate (70 mg, 260 μmol), TPP (65 mg, 260 μmol), and DIAD (50 mg, 260 μmol). Additional equivalents of TPP and DIAD were added at two 15 minute intervals, and the reaction mixture shaken for two hours. The resin was then washed with DMF (3×10 mL) and then with methanol (3×10 mL) and then dried in vacuo. The peptidylphosphonate was cleaved from the resin by treatment with 0.5 mL of TFA for 30 minutes.

EXAMPLE 7

Solid Phase Synthesis of Peptidylphosphonates 7.1 General Procedure

The methyl N-NPEOC-aminoalkylphosphonate (100 μmole), tris (4-chlorophenyl)phosphine (100 μmole) and diethylazodicarboxylate (100 μmole) were preactivated in anhydrous THF (900 μL) for 5 minutes. The mixture was then added to a resin (previously dried under vacuum in the presence of phosphorous pentoxide) containing a terminal hydroxyl group (≦20 μmole) that had been suspending in anhydrous THF (100 μL) and DIEA (200 μmole). The mixture was sonicated at 25° C. until the reaction was complete. The resin was then washed with NMP and ether and dried.

7.2 NPEOC-Deprotection and Coupling Efficiency Determination

The resin was treated with 5% DBU in NMP (1 mL) for 2 hours. The released 4-nitrostyrene was spectroscopically measured at 308 nm ($\epsilon = 1.32 \times 10^4$) to determine the coupling efficiency. The resin was washed with NMP and ether.

7.3 Capping

The resin was treated with commercially available capping reagents until negative ninhydrin tests were obtained.

7.4 Peptide Elongation

Uncapped peptidylphosphonate was further elongated using standard HBTU/HOBT amino acid coupling chemistry.

7.5 Deprotection and Cleavage of the Peptidylphosphonate

The resin bound peptidylphosphonate was treated with a 1:2:2 mixture of thiophenol:triethylamine:dioxane (1 mL) for 2 hours. However, if the phosphoryl methoxide group was to be retained, this treatment was not performed. Following washes with NMP, methanol, and ether, the peptidylphosphonate was treated with trifluoroacetic acid containing the appropriate scavengers (1 mL) for 1 hours.

7.6 Half-life Coupling Time Determination

Equal amounts of resin containing a terminal α-hydroxylalkyl acid were placed in separate containers then treated with the appropriate methyl N-NPEOC-aminoalkylphosphonate using the general procedure described above. After appropriate time intervals the resin in one container is washed as above then treated with 5% DBU/NMP and the coupling yield was determined. The coupling yields form each container at different time intervals was then plotted and the pseudo-first order rate constant calculated and used to determine the coupling time half-life.

7.7 Results

The following peptidylphosphonates, including both the phosphoryl methoxide and the phosphonic acid forms, have been synthesized and characterized: Z-(R,S)-Phe$^P$(O)-Leu-Ala-OH; Z-Gly$^P$(O)-Leu-Ala-OH; Z-(R)-Ala$^P$(O)-Leu-Ala-OH; Z-(R,S)-Leu$^P$(O)-Leu- Ala-OH; Z-(R,S)-Val$^P$(O)-Leu-Ala-OH, where Z represents CBz. The following phosphonic acids were also synthesized and characterized: Z-(R,S)-Phe$^P$(O)-Leu-Trp-OH; and Z-(R,S)-Phe$^P$(O)-Leu-Leu.

The K$_i$ values for thermolysin for the following peptidylphosphonates have also been determined: Z-Gly$^P$-(O)-Leu-Ala-OH, 13 μM; Z-(R)-Ala$^P$(O)-Leu-Ala-OH, 1.8 μM; Z-(R,S)-Leu$^P$(O)-Leu-Ala-OH, 680 nm/42 μM (L/D isomers); and Z-(R,S)-Phe$^P$(O)-Leu-Ala-OH, 45 nM/30 μM (L/D isomers).

7.8 Peptidylphosphonate Combinatorial Library Preparations

Figure 13:
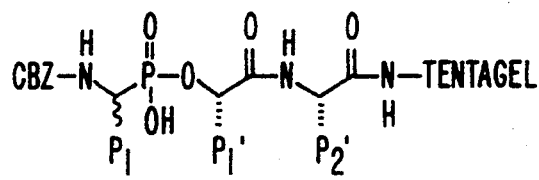
FIG. 13 depicts the monomer basis set used for the production of the peptidylphosphonate libraries described herein.
Figure 13:
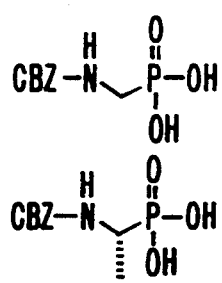
Figure 13:
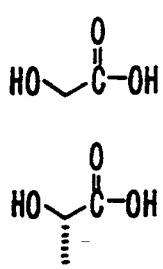
Figure 13:
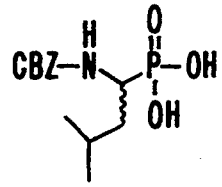
Figure 13:
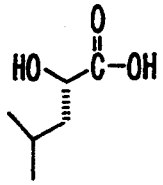
Figure 13:
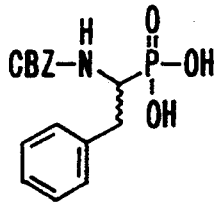
Figure 13:
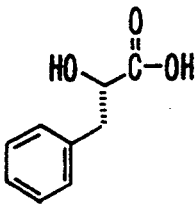
Figure 13:
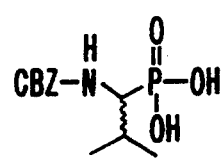
Figure 13:
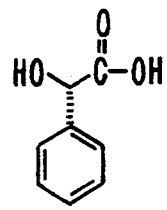
Figure 13:
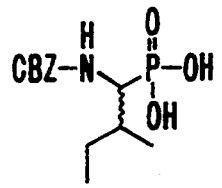
Figure 13:

The protocol shown in FIG. 10 using the monomer basis set shown in FIG. 13 was used to prepare a library of N-CBz capped peptidylphosphonates bound to Tentagel resin. This protocol is based on the "divide and pool" technology described by Furka et al. (1991) *Int. J. Pept. Protein Res.* 37:487, which is incorporated herein by reference.

EXAMPLE 8

Assay Protocols

8.Depletion Assays

Figure 14:
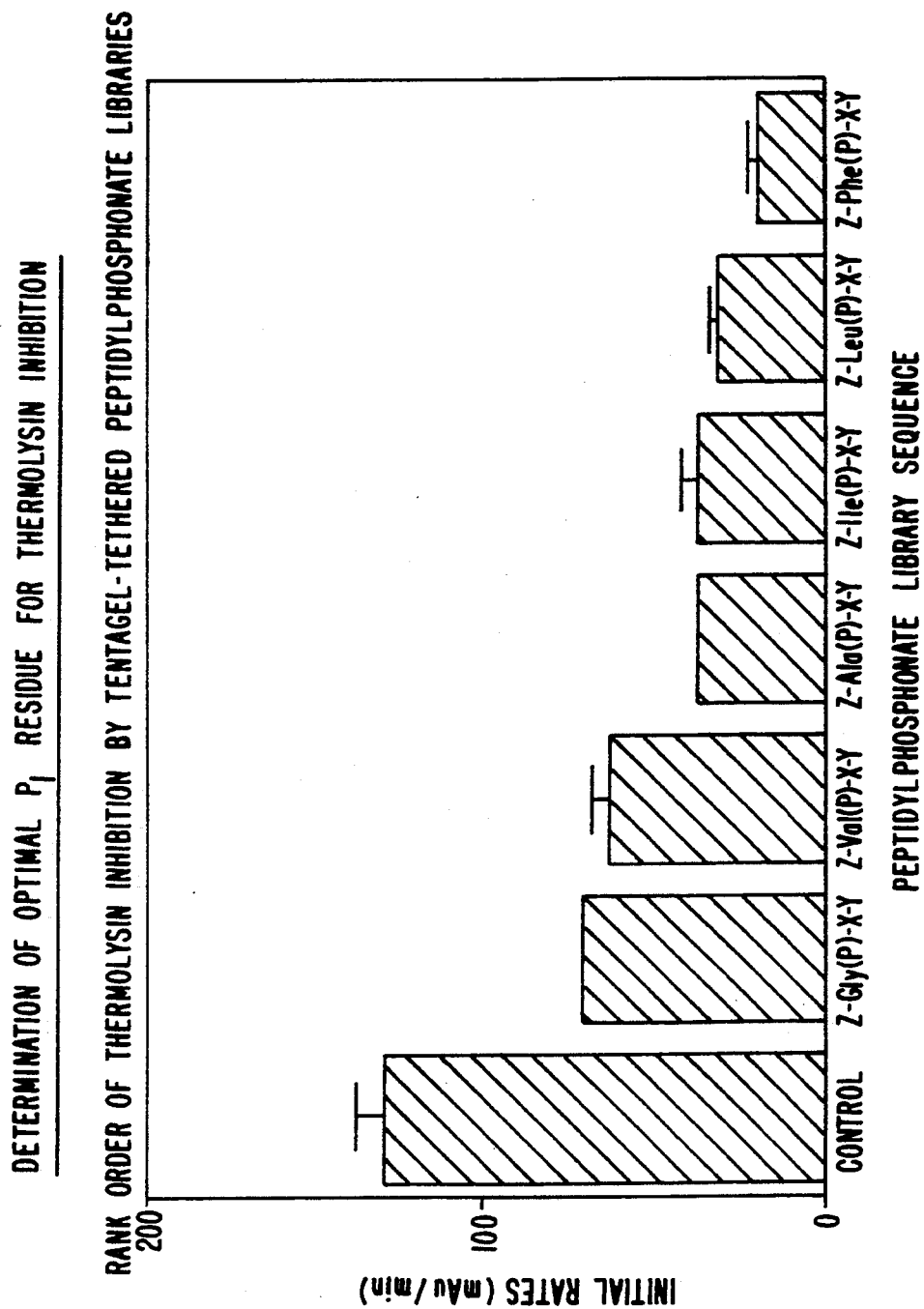
FIG. 14 is a graphic depiction of the rank order of thermolysin inhibition by tentagel-tethered peptidylphosphonates.

Resin bound inhibitor was pre-incubated with the enzyme thermolysin (100 nM). The support with resin bound inhibitor/enzyme complex was removed by filtration. An aliquot of the filtrate was treated with N-(3-[2-furyl]acryloyl)-Glu-Leu amide (1 mM). The turnover rate was analyzed in an attempt to rank order the binding affinities of the peptidylphosphonates. These results for a partial characterization of thermolysin's interactions with the peptidylphosponate libraries prepared in Example 7.8 above are shown in FIG. 14.

8.2 FITC-Thermolysin Binding Assay

The binding assay described above can be conducted using the FACS instrument to quantify the relative fluorescence activity. This format does require the use of small diameters with narrow size distribution.

We claim:

1. A method for preparing a phosphonic acid monoester from a phosphonate with a structure:

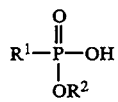

wherein R$^1$ is selected from the group consisting of alkyl, aryl, Substituted alkyl, substituted aryl, heteroaryl, alkylaryl, and aminoalkyl, and R$^2$ is selected from the group consisting of methyl, ethyl, benzyl, and substituted benzyl, by treating said phosphonate with a dialkylazodicarboxylate, a triarylphosphine, wherein at least one of the aryl groups of said triarylphosphine bears an electron withdrawing substituent, and a primary or secondary alcohol with a structure R$^3$OH, wherein R$^3$ is selected from the group consisting of alkyl, aryl, substituted alkyl, substituted aryl, and aminoalkyl, and an exogenous base in an aprotic solvent, to yield a phosphonate diester with a structure:

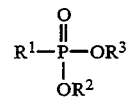

wherein R$^2$ and R$^3$ are not identical, and R$^2$ can be selectively hydrolyzed without hydrolyzing R$^3$, and then treating said phosphonate diester to hydrolyze selectively said phosphonate diester to yield said phosphonic acid monoester with a structure:

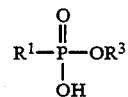

wherein said phosphonate is present in excess, said excess being greater than a ratio of 1.1 equivalents of phosphonate to one equivalent of alcohol.

2. The method of claim 1 wherein R$^2$ is methyl, said dialkylazodicarboxylate is diisopropylazodicarboxylate, and said triarylphosphine is tris(4-chlorophenyl)phosphine.

3. The method of claim 1 wherein said alcohol is a primary alcohol.

4. The method of claim 1 wherein said alcohol is a secondary alcohol.

5. The method of claim 1 wherein said phosphonate is an alpha-aminoalkylphosphonate.

6. The method of claim 5 wherein said alcohol is covalently linked to a solid support.

7. The method of claim 6, wherein said solid support is a bead or a particle.

8. The method of claim 6 wherein said solid support is prepared by treating a solid support to which an amino acid or peptide is covalently linked so as to have an amine group of said amino acid or peptide on a surface of said support with a hydroxy acid to couple said hydroxy acid to said amine group and to yield a hydroxy group covalently linked to said support.

9. The method of claim 8, wherein, after said hydroxy acid is coupled to said amine group, said support is treated with an alpha-aminoalkylphosphonate with the following structure:

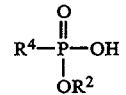

wherein R$^4$ is an alpha-aminoalkyl group, and R$^2$ is selected from the group consisting of methyl, ethyl, benzyl, and substituted benzyl;

a dialkylazodicarboxylate;

an exogenous base; and a triarylphosphine, wherein at least one of the aryl groups of said triarylphosphine bears an electron withdrawing substituent, to couple said alpha-aminoalkylphosphonate to said hydroxyl groups on said surface.

10. The method of claim 9, further comprising the step of treating said support with thiophenol and triethylamine whereby the R$^2$ group is selectively hydrolyzed.

11. The method of claim 10, further comprising the step of coupling an amino acid to the amino group of said alpha-aminoalkylphosphonate.

* * * * *